「 
US007993835B1

(12) United States Patent
Scholl et al.

(10) Patent No.: US 7,993,835 B1
(45) Date of Patent: Aug. 9, 2011

(54) BRCA2 MUTATIONS AND USE THEREOF

(75) Inventors: Thomas M. Scholl, W. Borough, MA (US); Brian E. Ward, Park City, UT (US); Amie Deffenbaugh, Salt Lake City, UT (US); Lynn Anne Burbidge, Salt Lake City, UT (US); Walter W. Noll, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 239 days.

(21) Appl. No.: 12/116,853

(22) Filed: May 7, 2008

Related U.S. Application Data

(60) Provisional application No. 60/917,581, filed on May 11, 2007, now abandoned.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6; 435/91.2; 536/23.5; 536/24.31
(58) Field of Classification Search ........................ None
See application file for complete search history.

(56) References Cited

U.S. PATENT DOCUMENTS 6,033,857 A * 3/2000 Tavtigian et al. ................. 435/6

OTHER PUBLICATIONS

Genecard for BRCA2, available via url: <genecards.org/cgi-bin/carddisp.pl?gene=brca2>, printed May 18, 2010.*
Langdahl et al. Journal of Bone and Mineral Research (2000) 15: 402-414.*
Wall. Nature Reviews Genetics (2003) 4: 587-597.*
Ioannidis et al. Nature Genetics (2001) 29:306-309.*
Hirschhorn et al. Genetics in Medicine. 2002. 4: 45-61.*
Halushka et al. Nature. Jul. 1999. 22: 239-247.*

* cited by examiner

*Primary Examiner* — Carla Myers
(74) *Attorney, Agent, or Firm* — Benjamin G. Jackson; Myriad Genetics IP Department

(57) ABSTRACT

Genetic variants in the BRCA2 gene are disclosed which are useful as diagnosis biomarkers.

7 Claims, No Drawings

BRCA2 MUTATIONS AND USE THEREOF

CROSS REFERENCE TO RELATED U.S. APPLICATIONS

This application claims the benefit of U.S. Provisional Application Ser. No. 60/917,581 filed on May 11, 2007, the entire content of which being incorporated herein by reference.

SEQUENCE LISTING

The instant application was filed without a formal Sequence Listing. A formal Sequence Listing in computer readable form has therefore been submitted electronically as a text file. This text file, which is named "3021-01-2U_2008-08-04_SEQ_LIST_(TXT)_ST25_BLC-BGJ.txt", was created on Aug. 4, 2008, and is 43,849 bytes in size. Its contents are incorporated by reference herein in their entirety.

FIELD OF THE INVENTION

This invention generally relates to molecular genetics, particularly to the identification of genetic variants that are associated with diseases, and methods of using the identified variants.

BACKGROUND OF THE INVENTION

Breast cancer susceptibility gene 2 (BRCA2) is a tumor suppressor gene identified on the basis of its genetic linkage to familial breast cancers. Mutations of the BRCA2 gene in humans are associated with predisposition to breast. In fact, BRCA1 and BRCA2 mutations are responsible for the majority of familial breast cancer. Inherited mutations in the BRCA1 and BRCA2 genes account for approximately 7-10% of all breast cancer cases. Women with BRCA mutations have a lifetime risk of breast cancer between 56-87%, and a lifetime risk of ovarian cancer between 27-44%. In addition, mutations in BRCA2 gene have also been linked to various other tumors including, e.g., pancreatic cancer.

A large number of deleterious mutations in BRCA2 gene have been discovered. Genetic testing on patients to determine the presence or absence of such deleterious mutations has proven to be an effective approach in detecting predispositions to breast and ovarian cancers. Genetic testing is now commonly accepted as the most accurate method for diagnosing hereditary breast cancer and ovarian risk.

As deleterious mutations in BRCA2 are associated with predisposition to cancers, particularly breast cancer and ovarian cancer, it is desirable to identify additional naturally existing deleterious mutations in the BRCA2 gene, which may serve as valuable diagnostic markers. However, a large number of genetic variants in BRCA2 gene have been found and the number continues to increase. Many of these variants are misense changes, inframe insertion or deletions, or intron/exon junction changes. Often, it is difficult to understand the effect of such variants, and they are typically reported as "uncertain variants" after genetic testing. There is great need in the art to reclassify such uncertain variants and determine whether they are deleterious mutations or merely clinically insignificant rare polymorphisms.

SUMMARY OF THE INVENTION

The present invention is based on the discovery of a number of genetic variants in the human BRCA2 gene and their clinical effect. The genetic variants are summarized in Table 1 below. The genetic variants are useful in detecting the presence or absence of a predisposition to BRCA2-associated cancer, particularly breast and ovarian cancers, as well as in diagnosing and prognosing BRCA2-associated cancer, particularly breast and ovarian cancers, and determining drug response and efficacy in patients.

Accordingly, in a first aspect of the present invention, an isolated human BRCA2 gene is provided containing at least one of the newly discovered genetic variants as summarized in Table 1 below. The present invention also provides isolated nucleic acids having a contiguous span of at least 18, 19, 20, 21, 22, 25 or 30, or at least 50 nucleotides of a human nucleic acid sequence, wherein the contiguous span encompasses and contains a nucleotide variant selected from those in Table 1.

DNA microchips or microarrays are also provided comprising an isolated human gene or an isolated oligonucleotide according to the present invention.

In accordance with another aspect of the invention, an isolated human protein or a fragment thereof is provided having a novel amino acid variant corresponding to a nucleotide variant in Table 1.

The present invention also provides an isolated antibody specifically immunoreactive with a human protein variant of the present invention.

In accordance with yet another aspect of the present invention, a method is provided for genotyping an individual by determining whether the individual has a nucleotide variant or an amino acid variant provided in accordance with the present invention. The individual can be a person without cancer or having been diagnosed of cancer, particularly breast or ovarian cancer.

In addition, a method is also provided for detecting in an individual the presence or absence of a predisposition to BRCA2-associated cancer, particularly breast and ovarian cancers, comprising genotyping the individual to determine the genotype at the variant locations discovered according to the present invention, particularly whether the individual has a nucleotide variant or an amino acid variant provided in accordance with the present invention, and determining the presence or absence of a predisposition to BRCA2-associated cancer, particularly breast and ovarian cancers based on the correlation between the variants and BRCA2-associated cancer, particularly breast and ovarian cancers discovered according to the present invention.

The present invention also provides a method for diagnosing BRCA2-associated cancer, particularly breast and ovarian cancers in an individual. The method comprises genotyping the individual to determine the genotype at the variant locations discovered according to the present invention, particularly whether the individual has a nucleotide variant or an amino acid variant provided in accordance with the present invention, and making a diagnosis of BRCA2-associated cancer, particularly breast and ovarian cancers based on the correlation between the variants and BRCA2-associated cancer, particularly breast and ovarian cancers discovered according to the present invention.

In yet another aspect, the present invention provides a method of treating or delaying the onset of BRCA2-associated cancer, particularly breast and ovarian cancers comprising identifying an individual having a nucleotide variant according to the present invention, and treating the individual with a suitable drug effective in treating or delaying the onset of BRCA2-associated cancer, particularly breast and ovarian cancers.

In yet another aspect, the invention provides a method of predicting an individual's response to therapeutic treatment.

This method may involve: (i) detecting in the individual the presence or absence of a genetic variant in one or more of the branch points of the present invention; and (ii) determining the individual's response to treatment based on the presence or absence of the genetic variant. The presence of a genetic variant in an individual may be determined by the methods described herein as well as those well known in the art. The method may be used to determine efficacy of various forms of drugs including, but not limited to, chemotherapeutics and inhibitors of the DNA damage repair pathway.

In accordance with another aspect of the invention, a detection kit is also provided for genotyping in an individual for the genotypes at the variant loci according to the present invention as summarized in Table 1. In a specific embodiment, the kit is used in predicting a predisposition to BRCA2-associated cancer, particularly breast and ovarian cancers in an individual. In another specific embodiment, the kit is used in diagnosing BRCA2-associated cancer, particularly breast and ovarian cancers in an individual. The kit may include, in a carrier or confined compartment, any nucleic acid probes or primers, or antibodies useful for detecting the nucleotide variants or amino acid variants of the present invention as described above. The kit can also include other reagents such as DNA polymerase, buffers, nucleotides and others that can be used in the method of detecting the variants according to this invention. In addition, the kit preferably also contains instructions for using the kit.

The foregoing and other advantages and features of the invention, and the manner in which the same are accomplished, will become more readily apparent upon consideration of the following detailed description of the invention taken in conjunction with the accompanying examples and drawings, which illustrate preferred and exemplary embodiments.

DETAILED DESCRIPTION OF THE INVENTION

1. Definitions

The terms "genetic variant," "nucleotide variant" and "mutations" are used herein interchangeably to refer to changes or alterations to the reference human genomic DNA or cDNA sequences at a particular locus, including, but not limited to, nucleotide base deletions, insertions, inversions, and substitutions in the coding and non-coding regions. Deletions may be of a single nucleotide base, a portion or a region of the nucleotide sequence of the gene, or of the entire gene sequence. Insertions may be of one or more nucleotide bases. The "genetic variant" or "nucleotide variants" may occur in transcriptional regulatory regions, untranslated regions of mRNA, exons, introns, or exon/intron junctions. The "genetic variant" or "nucleotide variants" may or may not result in stop codons, frame shifts, deletions of amino acids, altered gene transcript splice forms or altered amino acid sequence.

The term "allele" or "gene allele" is used herein to refer generally to a naturally occurring gene having a reference sequence or a gene containing a specific nucleotide variant.

As used herein, "haplotype" is a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human BRCA1 protein sequence resulting from "genetic variants" or "nucleotide variants" to the reference human gene encoding the reference BRCA1 protein. The term "amino acid variant" is intended to encompass not only single amino acid substitutions, but also amino acid deletions, insertions, and other significant changes of amino acid sequence in the reference BRCA1 protein.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

As used herein, the term "BRCA2 nucleic acid" means a nucleic acid molecule the nucleotide sequence of which is uniquely found in an BRCA2 gene. That is, a "BRCA2 nucleic acid" is either an BRCA2 genomic DNA or mRNA/cDNA, having a naturally existing nucleotide sequence encoding a naturally existing BRCA2 protein (wild-type or mutant form).

The term "locus" refers to a specific position or site in a gene sequence or protein. Thus, there may be one or more contiguous nucleotides in a particular gene locus, or one or more amino acids at a particular locus in a polypeptide. Moreover, "locus" may also be used to refer to a particular position in a gene where one or more nucleotides have been deleted, inserted, or inverted.

As used herein, the terms "polypeptide," "protein," and "peptide" are used interchangeably to refer to an amino acid chain in which the amino acid residues are linked by covalent peptide bonds. The amino acid chain can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The terms "primer", "probe," and "oligonucleotide" are used herein interchangeably to refer to a relatively short nucleic acid fragment or sequence. They can be DNA, RNA, or a hybrid thereof, or chemically modified analog or derivatives thereof. Typically, they are single-stranded. However, they can also be double-stranded having two complementing strands which can be separated apart by denaturation. In specific embodiments, the oligonucleotides can have a length of from about 8 nucleotides to about 200 nucleotides, or from about 12 nucleotides to about 100 nucleotides, or from about 18 to about 50 nucleotides. They can be labeled with detectable markers or modified in any conventional manners for various molecular biological applications.

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Specifically, since a naturally existing chromosome (or a viral equivalent thereof) includes a long nucleic acid sequence, an "isolated nucleic acid" as used herein means a nucleic acid molecule having only a portion of the nucleic acid sequence in the chromosome but not one or more other portions present on the same chromosome. More specifically, an "isolated nucleic acid" typically includes no more than 25 kb naturally occurring nucleic acid sequences which immediately flank the nucleic acid in the naturally existing chromosome (or a viral equivalent thereof). However, it is noted that an "isolated nucleic acid" as used herein is distinct from a clone in a conventional library such as genomic DNA library and cDNA library in that the clone in a library is still in admixture with almost all the other nucleic acids of a chromosome or cell. Thus, an "isolated nucleic acid" as used herein also should be substantially separated from other naturally occurring nucleic acids that are on a different chromosome of the same organism. Specifically, an "isolated nucleic acid" means a composition in which the specified nucleic acid molecule is significantly enriched so as to constitute at least 10% of the total nucleic acids in the composition.

An "isolated nucleic acid" can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed), or can be a chemically synthesized nucleic acid having a naturally occurring nucleotide sequence or an artificially modified form thereof.

The term "isolated polypeptide" as used herein is defined as a polypeptide molecule that is present in a form other than that found in nature. Thus, an isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a composition or preparation in which the specified polypeptide molecule is significantly enriched so as to constitute at least 10% of the total protein content in the composition. A "purified polypeptide" can be obtained from natural or recombinant host cells by standard purification techniques, or by chemically synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally occurring polypeptide or isolated polypeptide having a specified polypeptide molecule covalently linked to one or more other polypeptide molecules that do not link to the specified polypeptide in nature. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

The term "high stringency hybridization conditions," when used in connection with nucleic acid hybridization, means hybridization conducted overnight at 42 degrees C. in a solution containing 50% formamide, 5×SSC (750 mM NaCl, 75 mM sodium citrate), 50 mM sodium phosphate, pH 7.6, 5× Denhardt's solution, 10% dextran sulfate, and 20 microgram/ml denatured and sheared salmon sperm DNA, with hybridization filters washed in 0.1×SSC at about 65° C. The term "moderate stringency hybridization conditions," when used in connection with nucleic acid hybridization, means hybridization conducted overnight at 37 degrees C. in a solution containing 50% formamide, 5×SSC (750 mM NaCl, 75 mM sodium citrate), 50 mM sodium phosphate, pH 7.6, 5× Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific "percentage identical to" another sequence (comparison sequence) in the present disclosure. In this respect, the percentage identity is determined by the algorithm of Karlin and Altschul, *Proc. Natl. Acad. Sci. USA*, 90:5873-5877 (1993), which is incorporated into various BLAST programs. Specifically, the percentage identity is determined by the "BLAST 2 Sequences" tool, which is available at NCBI's website. See Tatusova and Madden, *FEMS Microbiol. Lett.*, 174(2):247-250 (1999). For pairwise DNA-DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter). Percent identity of two sequences is calculated by aligning a test sequence with a comparison sequence using BLAST 2.1.2., determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST 2.1.2 is used to compare two sequences, it aligns the sequences and yields the percent identity over defined, aligned regions. If the two sequences are aligned across their entire length, the percent identity yielded by the BLAST 2.1.1 is the percent identity of the two sequences. If BLAST 2.1.2 does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence.

As used herein the term "linkage disequilibrium," or "LD," means that there is interdependence between alleles at loci closely positioned within a genome. More precisely, LD means that the probability to find allele A at locus 1 depends on whether allele B is present at locus 2. Complete LD means that alleles A and B are always found together. Pitchard and Przeworski, *Am. J. Hum. Genet.*, 69:1-4 (2001) teaches a widely used measure of LD:

$$r^2 = (P(AB) - P(A)P(B))^2 / P(A)P(a)P(B)P(b),$$

where A and a are two alleles at locus 1, B and b are two alleles at locus 2, and P(X) is the probability of X.

If LD is absent, then P(AB)=P(A)P(B), and, therefore, $r^2$=0. In contrast, in the case of complete disequilibrium, P(AB)=P(A)=P(B), and, therefore, $r^2$=1. In the case of partial LD, $r^2$ is between 0 and 1, and high values of $r^2$ correspond to strong LD. If allele A of locus 1 is associated with a disease, and there is a strong LD between locus 1 and locus 2, so that P(AB)>P(A)P(B), then allele B is associated with the disease too. To define strong LD, a threshold of $r^2$>0.8 is usually used.

See Carlson et al, *Nat. Genet.*, 33(4):518-21 (2003). This threshold has been applied in identifying additional variants that are in LD with the disease, disorder or phenotype-associated SNP of the instant invention.

Thus, when a second nucleotide variant is said herein to be in linkage disequilibrium, or LD, with a first nucleotide variant, it is meant that a second variant is closely dependent upon a first variant, with a $r^2$ value of at least 0.8, as calculated by the formula above. Thus, the term "LD variants" as used herein means variants that are in linkage disequilibrium with an $r^2$ value of at least 0.8.

The term "reference sequence" refers to a polynucleotide or polypeptide sequence known in the art, including those disclosed in publicly accessible databases, e.g., GenBank, or a newly identified gene sequence, used simply as a reference with respect to the nucleotide variants provided in the present invention. The nucleotide or amino acid sequence in a reference sequence is contrasted to the alleles disclosed in the present invention having newly discovered nucleotide or amino acid variants. Smith and coworkers described the complete genomic sequence of a 117 kilobase region of human DNA containing the BRCA2 gene, and deposited the nucleotide sequence of the genomic DNA in the GenBank under the Accession Number Z74739 and Z73359 (Smith et al., *Genome Res.*, 6:1029-1049 (1996)). This nucleotide sequence (referred to as Z74739 and Z73359) is used herein as a reference sequence for identifying the polymorphic positions of the large rearrangements of the present invention.

The nucleotide and amino acid sequences in GenBank Accession No. U43746 are used as the reference sequences for BRCA2 cDNA and proteins, respectively.

2. Nucleotide and Amino Acid Variants

In accordance with the present invention, analysis of the nucleotide sequence of genomic DNA corresponding to the BRCA2 genes of specific human patients has led to the discovery of a number of mutant BRCA2 alleles and characterization of the effect of such variants. A previously known genomic sequence of the BRCA2 gene is disclosed in the GenBank under the Accession Nos. Z74739 (exons 2-24) and Z73359 (exons 25-27). A complete cDNA sequence of the BRCA2 gene and the amino acid sequence of the BRCA2 polypeptide encoded by the cDNA sequence are set forth in the GenBank under the Accession No. U43746. The cDNA sequence is used herein as the reference sequence for identifying the positions of the nucleotide variants of the present invention in exons. The cDNA sequence and the genomic sequence are used in conjunction to identify the variant positions in introns. In addition, the amino acid sequence in GenBank Accession No. U43746 is used as a reference sequence for identifying the amino acid variants of the present invention.

The positions are assigned by aligning the variant allele sequences to the above-identified cDNA and/or genomic reference sequences, with the starting nucleotide (nucleotide +1) being the A in the start codon ATG in the reference cDNA sequence. The positions in an intron or intervening sequence (IVS) are assigned relative to the exon immediately preceding or following the intron. Thus, for example, IVS3+31C>T means a nucleotide variant T (in contrast to C in the reference sequence) at the 31$^{st}$ nucleotide position counting from the first nucleotide of the intron (or IVS) 3 immediately following the exon immediately preceding the intron, i.e., exon 3. IVS6−29C>A means a nucleotide polymorphism of A (in contrast to C in the reference sequence) at the 29$^{th}$ nucleotide position counting in the downstream to upstream direction from the intronic nucleotide immediately preceding exon 7. In other words, positive numbers start from the G of the donor site invariant GT, while negative numbers start from the G of the acceptor site invariant AG. The amino acid substitutions caused by the nucleotide variants are also identified according to conventional practice. For example, A160V means the amino acid variant at position 160 is V in contrast to A in the reference sequence.

The genetic variants are summarized in Tables 1-2 below. Exemplary sequences spanning the genetic variants in the table are provided in Table 3 below.

TABLE 1

Deleterious BRCA2 Variants

| Exon | Variant | Effect | cDNA Position | Original Base | Deleted/ Inserted/ New Base | SEQ ID NO |
|---|---|---|---|---|---|---|
| 3 | 473delAA | deleterious | 473 | A | AA | 1 |
| 3 | Q66X | deleterious | 424 | C | T | 2 |
| 3 | E97X | deleterious | 517 | G | T | 3 |
| 3 | 389delA | deleterious | 389 | A | A | 4 |
| 4 | 570delTA | deleterious | 570 | T | TA | 5 |
| 4 | 638ins8 | deleterious | 638 | C | | 6 |
| 5 | 699delG | deleterious | 699 | G | G | 7 |
| 5 | 697delAA | deleterious | 697 | A | AA | 8 |
| 6 | 719delT | deleterious | 719 | T | T | 9 |
| 7 | 750delT | deleterious | 750 | T | T | 10 |
| 7 | 762delA | deleterious | 762 | A | A | 11 |
| 10 | 2121delT | deleterious | 2,121 | T | T | 12 |
| 10 | 1756delGA | deleterious | 1,756 | G | GA | 13 |
| 10 | 2074delT | deleterious | 2,074 | T | T | 14 |
| 10 | 1074delCA | deleterious | 1,074 | C | CA | 15 |
| 10 | 2027del6 | deleterious | 2,027 | A | | 16 |
| 10 | 1994insA | deleterious | 1,994 | A | A | 17 |
| 10 | 1187insT | deleterious | 1,187 | T | T | 18 |
| 10 | L583X | deleterious | 1,976 | T | A | 19 |
| 10 | S424X | deleterious | 1,499 | C | G | 20 |
| 10 | 1536delGA | deleterious | 1,536 | G | GA | 21 |
| 10 | Q407X | deleterious | 1,447 | C | T | 22 |
| 10 | 1836delTG | deleterious | 1,836 | T | TG | 23 |
| 10 | S611X | deleterious | 2,060 | C | G | 24 |
| 10 | S273X | deleterious | 1,046 | C | A | 25 |
| 11 | 6239del7 | deleterious | 6,239 | A | | 26 |
| 11 | Q1295X | deleterious | 4,111 | C | T | 27 |
| 11 | 6625insT | deleterious | 6,625 | T | T | 28 |
| 11 | 2403insA | deleterious | 2,403 | A | A | 29 |
| 11 | K1638X | deleterious | 5,140 | A | T | 30 |
| 11 | Y1672X | deleterious | 5,244 | C | G | 31 |
| 11 | 6677delAA | deleterious | 6,677 | A | AA | 32 |
| 11 | 7044delAA | deleterious | 7,044 | A | AA | 33 |
| 11 | 3551delA | deleterious | 3,551 | A | A | 34 |
| 11 | 4688delAA | deleterious | 4,688 | A | AA | 35 |
| 11 | 3458ins5 | deleterious | 3,458 | T | | 36 |
| 11 | 5562del7 | deleterious | 5,562 | T | | 37 |
| 11 | X1290ins (4096ins3) | deleterious | 4,096 | T | AAT | 38 |
| 11 | 4951delG | deleterious | 4,951 | G | G | 39 |
| 11 | 5469insTA | deleterious | 5,469 | C | TA | 40 |
| 11 | K757X | deleterious | 2,497 | A | T | 41 |
| 11 | K1531X | deleterious | 4,819 | A | T | 42 |
| 11 | 6708delA | deleterious | 6,708 | A | A | 43 |
| 11 | 4633del5 | deleterious | 4,633 | G | | 44 |
| 11 | 6662del8 | deleterious | 6,662 | A | | 45 |
| 11 | S648X | deleterious | 2,171 | C | G | 46 |
| 11 | 3948delGT | deleterious | 3,948 | G | GT | 47 |
| 11 | 5859delC | deleterious | 5,859 | C | C | 48 |
| 11 | 6088delA | deleterious | 6,088 | A | A | 49 |
| 11 | 3060del4 | deleterious | 3,060 | A | AAAA | 50 |
| 11 | C717X | deleterious | 2,379 | T | A | 51 |
| 11 | 3421delA | deleterious | 3,421 | A | A | 52 |
| 11 | 3586delG | deleterious | 3,586 | G | G | 53 |
| 11 | 5435delAA | deleterious | 5,435 | A | AA | 54 |
| 11 | 3237delCA | deleterious | 3,237 | C | CA | 55 |
| 11 | 5419delC | deleterious | 5,419 | C | C | 56 |
| 11 | 3305delA | deleterious | 3,305 | A | A | 57 |
| 11 | S1385X | deleterious | 4,382 | C | G | 58 |

TABLE 1-continued

Deleterious BRCA2 Variants

| Exon | Variant | Effect | cDNA Position | Original Base | Deleted/Inserted/New Base | SEQ ID NO |
|---|---|---|---|---|---|---|
| 11 | Y2222X | deleterious | 6,894 | C | G | 59 |
| 11 | 6070ins8 | deleterious | 6,070 | G | | 60 |
| 11 | 6662delA | deleterious | 6,662 | A | A | 61 |
| 11 | 6415del11 | deleterious | 6,415 | G | | 62 |
| 11 | 2886delTG | deleterious | 2,886 | T | TG | 63 |
| 11 | 6319insA | deleterious | 6,319 | A | A | 64 |
| 11 | 5344del4 | deleterious | 5,344 | A | AATA | 65 |
| 11 | 4994delC | deleterious | 4,994 | C | C | 66 |
| 11 | 5667insT | deleterious | 5,667 | T | T | 67 |
| 11 | 6616del5 | deleterious | 6,616 | T | | 68 |
| 11 | 5897del5 | deleterious | 5,897 | T | | 69 |
| 11 | 4637del5 | deleterious | 4,637 | T | | 70 |
| 11 | 6287del4 | deleterious | 6,287 | A | AACA | 71 |
| 11 | G1712X | deleterious | 5,362 | G | T | 72 |
| 11 | 7044del5 | deleterious | 7,044 | A | | 73 |
| 11 | 6310del5 | deleterious | 6,310 | G | | 74 |
| 11 | L1053X | deleterious | 3,386 | T | G | 75 |
| 11 | 5008delA | deleterious | 5,008 | A | A | 76 |
| 11 | 6910insG | deleterious | 6,910 | G | G | 77 |
| 11 | 6886del5 | deleterious | 6,886 | G | | 78 |
| 11 | 3073delT | deleterious | 3,073 | T | T | 79 |
| 11 | 2482del4 | deleterious | 2,482 | G | GACT | 80 |
| 13 | 7230delC | deleterious | 7,230 | C | C | 81 |
| 14 | 7570delAA | deleterious | 7,570 | A | AA | 82 |
| 14 | Q2345X | deleterious | 7,261 | C | T | 83 |
| 14 | 7614delC | deleterious | 7,614 | C | C | 84 |
| 14 | Q2435X | deleterious | 7,531 | C | T | 85 |
| 14 | Q2456X | deleterious | 7,594 | C | T | 86 |
| 14 | E2420X | deleterious | 7,486 | G | T | 87 |
| 15 | Q2501X | deleterious | 7,729 | C | T | 88 |
| 15 | 7777ins8 | deleterious | 7,777 | A | | 89 |
| 15 | 7794insT | deleterious | 7,794 | T | T | 90 |
| 16 | 7932insT | deleterious | 7,932 | T | T | 91 |
| 16 | E2598X | deleterious | 8,020 | G | T | 92 |
| 16 | E2599X | deleterious | 8,023 | G | T | 93 |
| 16 | 7895insAA | deleterious | 7,895 | A | AA | 94 |
| 16 | 7884del4 | deleterious | 7,884 | T | TAAC | 95 |
| 16 | 8009insA | deleterious | 8,009 | A | A | 96 |
| 16 | Q2580X | deleterious | 7,966 | C | T | 97 |
| 17 | W2626X | deleterious | 8,106 | G | A | 98 |
| 18 | 8276insT | deleterious | 8,276 | C | T | 99 |
| 18 | 8513delC | deleterious | 8,513 | C | C | 100 |
| 18 | 8281delA | deleterious | 8,281 | A | A | 101 |
| 18 | 8292delCT | deleterious | 8,292 | C | CT | 102 |
| 19 | R2799X | deleterious | 8,623 | A | T | 103 |
| 19 | W2788X | deleterious | 8,591 | G | A | 104 |
| 21 | Q2899X | deleterious | 8,923 | C | T | 105 |
| 22 | W2970X | deleterious | 9,137 | G | A | 106 |
| 22 | 9045del4 | deleterious | 9,045 | G | GAAA | 107 |
| 22 | 9079insGG | deleterious | 9,079 | G | GG | 108 |
| 22 | S2984X | deleterious | 9,179 | C | G | 109 |
| 23 | 9225delGT | deleterious | 9,225 | G | GT | 110 |
| 23 | 9288delT | deleterious | 9,288 | T | T | 111 |
| 23 | L2996X | deleterious | 9,215 | T | A | 112 |
| 23 | 9324ins19 | deleterious | 9,324 | A | | 113 |
| 23 | S2994X | deleterious | 9,209 | C | G | 114 |
| 23 | W2990X | deleterious | 9,198 | G | A | 115 |
| 23 | 9193delA | deleterious | 9,193 | A | A | 116 |
| 24 | E3043X | deleterious | 9,355 | G | T | 117 |
| 24 | 9455delG | deleterious | 9,455 | G | G | 118 |
| 25 | 9489ins7 | deleterious | 9,489 | T | | 119 |
| 25 | 9645ins4 | deleterious | 9,645 | T | ATTT | 120 |
| 25 | IVS25+1insG | deleterious | 9,729 | G | G | 121 |
| 25 | S3094X | deleterious | 9,509 | C | G | 122 |
| 25 | 9637insA | deleterious | 9,637 | A | A | 123 |
| 25 | 9641insT | deleterious | 9,641 | T | T | 124 |
| 25 | 9604delC | deleterious | 9,604 | C | C | 125 |
| 25 | 9558insT | deleterious | 9,558 | T | T | 126 |
| 6 | K172N (744G>T) | deleterious | 744 | G | T | 127 |
| 8 | 900del33 | deleterious | 900 | T | | 128 |
| 12 | IVS12+1G>A | deleterious | 7,165 | g | A | 129 |
| 13 | IVS12−2A>C | deleterious | 7,166 | a | C | 130 |
| 18 | IVS18+2T>C | deleterious | 8,559 | t | C | 131 |
| 20 | IVS19−1G>A | deleterious | 8,716 | g | A | 132 |

TABLE 2

Polymorphic BRCA2 Variant

| Exon No. | Variant | Effect | cDNA Position | Original Base | Deleted/Inserted/New Base | SEQ ID NO |
|---|---|---|---|---|---|---|
| 2 | IVS1−14C>T | polymorphism | 190 | c | T | 133 |
| 2 | IVS1−10T>C | polymorphism | 190 | t | C | 134 |
| 3 | N60S | polymorphism | 407 | A | G | 135 |
| 4 | IVS3−19del8 | polymorphism | 545 | a | | 136 |
| 10 | S489C | polymorphism | 1,694 | C | G | 137 |
| 10 | K513R | polymorphism | 1,766 | A | G | 138 |
| 10 | A487E | polymorphism | 1,688 | C | A | 139 |
| 10 | Q347R | polymorphism | 1,268 | A | G | 140 |
| 11 | F2058C | polymorphism | 6,401 | T | G | 141 |
| 11 | G1529R | polymorphism | 4,813 | G | A | 142 |
| 11 | I1929V | polymorphism | 6,013 | A | G | 143 |
| 11 | L1904V | polymorphism | 5,938 | C | G | 144 |
| 11 | S2152Y | polymorphism | 6,683 | C | A | 145 |
| 11 | L929S | polymorphism | 3,014 | T | C | 146 |
| 11 | N9871 | polymorphism | 3,188 | A | T | 147 |
| 11 | R2108H | polymorphism | 6,551 | G | A | 148 |
| 11 | H2074N | polymorphism | 6,448 | C | A | 149 |
| 11 | Q1396R | polymorphism | 4,415 | A | G | 150 |
| 11 | V2138F | polymorphism | 6,640 | G | T | 151 |
| 11 | K1690N | polymorphism | 5,298 | A | C | 152 |
| 11 | M1149V | polymorphism | 3,673 | A | G | 153 |
| 11 | C1365Y | polymorphism | 4,322 | G | A | 154 |
| 11 | N900D | polymorphism | 2,926 | A | G | 155 |
| 11 | I1349T | polymorphism | 4,274 | T | C | 156 |
| 11 | Y1313C | polymorphism | 4,166 | A | G | 157 |
| 12 | D2312V | polymorphism | 7,163 | A | T | 158 |
| 14 | Q2384K | polymorphism | 7,378 | C | A | 159 |
| 15 | IVS14−14T>G | polymorphism | 7,664 | t | G | 160 |
| 16 | IVS15−15del4 | polymorphism | 7,846 | g | GTTT | 161 |
| 22 | IVS21−18T>C | polymorphism | 8,983 | t | C | 162 |
| 24 | IVS23−18T>C | polymorphism | 9,346 | t | C | 163 |
| 24 | K3059E | polymorphism | 9,403 | A | G | 164 |
| 25 | IVS25+9A>C | polymorphism | 9,729 | a | C | 165 |
| 26 | P3194Q | polymorphism | 9,809 | C | A | 166 |
| 27 | N3329S | polymorphism | 10,214 | A | G | 167 |
| 27 | F3362L | polymorphism | 10,312 | T | C | 168 |
| 27 | L3352V | polymorphism | 10,282 | C | G | 169 |
| 27 | S3396N | polymorphism | 10,415 | G | A | 170 |
| 27 | K3416T | polymorphism | 10,475 | A | C | 171 |
| 27 | I3418M | polymorphism | 10,482 | C | G | 172 |
| 10 | S384F | polymorphism | 1,379 | C | T | 173 |
| 10 | S326R | polymorphism | 1,206 | C | A | 174 |
| 10 | I505T | polymorphism | 1,742 | T | C | 175 |
| 10 | D596H | polymorphism | 2,014 | G | C | 176 |
| 10 | E462G | polymorphism | 1,613 | A | G | 177 |
| 11 | D935N | polymorphism | 3,031 | G | A | 178 |
| 11 | H2116R | polymorphism | 6,575 | A | G | 179 |
| 11 | T1414M | polymorphism | 4,469 | C | T | 180 |
| 11 | C1290Y | polymorphism | 4,097 | G | A | 181 |
| 11 | N986S | polymorphism | 3,185 | A | G | 182 |
| 11 | G1771D | polymorphism | 5,540 | G | A | 183 |
| 11 | D1902N | polymorphism | 5,932 | G | A | 184 |
| 14 | N2436I | polymorphism | 7,535 | A | T | 185 |
| 15 | T2515I | polymorphism | 7,772 | C | T | 186 |
| 18 | A2717S | polymorphism | 8,377 | G | T | 187 |
| 18 | D2665G | polymorphism | 8,222 | A | G | 188 |
| 20 | E2856A | polymorphism | 8,795 | A | C | 189 |
| 20 | S2835P | polymorphism | 8,731 | T | C | 190 |

TABLE 2-continued

Polymorphic BRCA2 Variant

| Exon No. | Variant | Effect | cDNA Position | Original Base | Deleted/ Inserted/ New Base | SEQ ID NO |
|---|---|---|---|---|---|---|
| 22 | K2950N | polymorphism | 9,078 | G | T | 191 |
| 23 | T3013I | polymorphism | 9,266 | C | T | 192 |

The genetic variants are indicated in Tables 1-2 by their positions and nucleotide and/or amino acid changes. The nucleotide sequences surrounding each of the genetic variants are provided in SEQ ID NOs:1-192 as indicated in Tables 1-2 above. However, it is noted that the nucleotide variants of the present invention are by no means limited to be only in the context of the sequences in the sequence listings or the particular position referred to herein. Rather, it is recognized that GenBank sequences may contain unrecognized sequence errors only to be corrected at a later date, and additional gene variants may be discovered in the future. The present invention encompasses nucleotide variants as referred to in Tables 1-2 irrespective of such sequence contexts. Indeed, even if the GenBank entries referred to herein are changed based on either error corrections or additional variants discovered, skilled artisans apprised of the present disclosure would still be able to determine or analyze the nucleotide variants of the present invention in the new sequence contexts.

3. Isolated Nucleic Acids

Accordingly, the present invention provides an isolated BRCA2 nucleic acid containing at least one of the newly discovered nucleotide variants as summarized in Tables 1-2. The term "BRCA2 nucleic acid" is inclusive and may be in the form of either double-stranded or single-stranded nucleic acids, and a single strand can be either of the two complementing strands. The isolated BRCA2 nucleic acid can be naturally existing genomic DNA, mRNA or cDNA. In one embodiment, the isolated BRCA2 nucleic acid has a nucleotide sequence according to SEQ ID NO:1-192 containing one or more exonic nucleotide variants of Table 1, or the complement thereof.

The present invention also provides an isolated nucleic acid, naturally occurring or artificial, having a nucleotide sequence that is at least 95%, preferably at least 97% and more preferably at least 99% identical to one of SEQ ID NOs:1-192 except for containing one or more nucleotide variants of Tables 1-2 and/or one or more LD variants thereof in Tables 1-2, or the complement thereof.

Also encompassed are isolated nucleic acids obtainable by:
(a) providing a human genomic library;
(b) screening the genomic library using a probe having a nucleotide sequence according to any one of SEQ ID NOs:1-192; and
(c) producing a genomic DNA comprising a contiguous span of at least 30 nucleotides of any one of SEQ ID NOs:1-192, wherein the genomic DNA thus produced contains one or more of the variants of the present invention in Tables 1-2 and/or one or more LD variants in Tables 1-2.

The present invention also includes isolated nucleic acids obtainable by:
(i) providing a cDNA library using human mRNA from a human tissue, e.g., blood;
(ii) screening the cDNA library using a probe having a nucleotide sequence according to any one of SEQ ID NOs:1-192; and
(iii) producing a cDNA DNA comprising a contiguous span of at least 30 nucleotides of any one of SEQ ID NOs:1-192, wherein the cDNA thus produced contains one or more of the nucleotide variants of the present invention in Tables 1-2 and/or one or more LD variants in Tables 1-2.

The present invention also encompasses an isolated nucleic acid comprising the nucleotide sequence of a region of a genomic DNA or cDNA or mRNA, wherein the region contains one or more nucleotide variants as provided in Tables 1-2 above, or an LD variant in Tables 1-2, or the complement thereof. Such regions can be isolated and analyzed to efficiently detect the nucleotide variants of the present invention. Also, such regions can also be isolated and used as probes or primers in detection of the nucleotide variants of the present invention and other uses as will be clear from the descriptions below.

Thus, in one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of a human nucleic acid, the contiguous span containing one or more nucleotide variants of Tables 1-2, and/or one or more LD variant in Tables 1-2, or the complement thereof. In specific embodiments, the isolated nucleic acids are oligonucleotides having a contiguous span of from about 17, 18, 19, 20, 21, 22, 23 or 25 to about 30, 40 or 50, preferably from about 21 to about 30 nucleotide residues, of any human nucleic acid, said contiguous span containing one or more nucleotide variants of Tables 1-2.

In one embodiment, the isolated nucleic acid comprises a contiguous span of at least 12, 15, 17, 18, 19, 20, 21, 22, 23, 24, 25, 26, 27, 28, 29, 30, 40, 50, 70 or 100 nucleotide residues of any one of SEQ ID NOs:1-192, containing one or more nucleotide variants of Tables 1-2, or the complement thereof. In specific embodiments, the isolated nucleic acid comprises a nucleotide sequence according to any one of SEQ ID NOs: 1-192, or the complements thereof. In preferred embodiments, the isolated nucleic acids are oligonucleotides having a contiguous span of from about 17, 18, 19, 20, 21, 22, 23 or 25 to about 30, 40 or 50, preferably from about 21 to about 30 nucleotide residues, of any one of SEQ ID NOs:1-192 and containing one or more nucleotide variants selected from those in Tables 1-2, or the complements thereof. The complements of the isolated nucleic acids are also encompassed by the present invention.

In preferred embodiments, an isolated oligonucleotide of the present invention is specific to an allele ("allele-specific") containing one or more nucleotide variants as disclosed in the present invention, or the complement thereof. That is, the isolated oligonucleotide is capable of selectively hybridizing, under high stringency conditions generally recognized in the art, to a genomic or cDNA or mRNA containing one or more nucleotide variants as disclosed in Tables 1-2, but not to a genomic or cDNA or mRNA having an alternative nucleotide variant at the same locus or loci. Such oligonucleotides will be useful in a hybridization-based method for detecting the nucleotide variants of the present invention as described in details below. An ordinarily skilled artisan would recognize various stringent conditions which enable the oligonucleotides of the present invention to differentiate between different alleles at the same variant locus. For example, the hybridization can be conducted overnight in a solution containing 50% formamide, 5×SSC, pH7.6, 5× Denhardt's solution, 10% dextran sulfate, and 20 microgram/ml denatured, sheared salmon sperm DNA. The hybridization filters can be washed in 0.1×SSC at about 65° C. Alternatively, typical PCR conditions employed in the art with an annealing temperature of about 55° C. can also be used.

In the isolated oligonucleotides containing a nucleotide variant according to the present invention, the nucleotide variant (or the complement thereof) can be located in any position. In one embodiment, a nucleotide variant (or the complement thereof) is at the 5' or 3' end of the oligonucleotides. In a more preferred embodiment, an oligonucleotide contains only one nucleotide variant from Tables 1-2 (or the complement thereof) according to the present invention, which is located at the 3' end of the oligonucleotide. In another embodiment, a nucleotide variant (or the complement thereof) of the present invention is located within no greater than four (4), preferably no greater than three (3), and more preferably no greater than two (2) nucleotides of the center of the oligonucleotide of the present invention. In more preferred embodiment, a nucleotide variant (or the complement thereof) is located at the center or within one (1) nucleotide of the center of the oligonucleotide. For purposes of defining the location of a nucleotide variant in an oligonucleotide, the center nucleotide of an oligonucleotide with an odd number of nucleotides is considered to be the center. For an oligonucleotide with an even number of nucleotides, the bond between the two center nucleotides is considered to be the center.

In other embodiments of the present invention, isolated nucleic acids are provided which encode a contiguous span of at least 6, 7, 8, 9, 10, 11, 12, 13, 14, 15, 16 or 17 amino acids of a protein wherein said contiguous span contains at least one amino acid variant in Tables 1-2 according to the present invention.

The oligonucleotides of the present invention can have a detectable marker selected from, e.g., radioisotopes, fluorescent compounds, enzymes, or enzyme co-factors operably linked to the oligonucleotide. The oligonucleotides of the present invention can be useful in genotyping as will be apparent from the description below.

In addition, the present invention also provides nucleic acid microchips or microarray incorporating one or more variant genomic DNA or cDNA or mRNA or an oligonucleotide according to the present invention. The microchips will allow rapid genotyping and/or haplotyping in a large scale efficiently. The microchips are also useful in determining quantitatively or qualitatively the expression of particularly variant alleles.

As is known in the art, in microchips, a large number of different nucleic acid probes are attached or immobilized in an array on a solid support, e.g., a silicon chip or glass slide. Target nucleic acid sequences to be analyzed can be contacted with the immobilized oligonucleotide probes on the microchip. See Lipshutz et al., *Biotechniques*, 19:442-447 (1995); Chee et al., *Science*, 274:610-614 (1996); Kozal et al., *Nat. Med.* 2:753-759 (1996); Hacia et al., *Nat. Genet.*, 14:441-447 (1996); Saiki et al., *Proc. Natl. Acad. Sci. USA*, 86:6230-6234 (1989); Gingeras et al., *Genome Res.*, 8:435-448 (1998). The microchip technologies combined with computerized analysis tools allow large-scale high throughput screening. See, e.g., U.S. Pat. No. 5,925,525 to Fodor et al; Wilgenbus et al., *J. Mol. Med.*, 77:761-786 (1999); Graber et al., *Curr. Opin. Biotechnol.*, 9:14-18 (1998); Hacia et al., *Nat. Genet.*, 14:441-447 (1996); Shoemaker et al., *Nat. Genet.*, 14:450-456 (1996); DeRisi et al., *Nat. Genet.*, 14:457-460 (1996); Chee et al., *Nat. Genet.*, 14:610-614 (1996); Lockhart et al., *Nat. Genet.*, 14:675-680 (1996); Drobyshev et al., *Gene*, 188: 45-52 (1997).

In a preferred embodiment, a DNA microchip is provided having a plurality of from 2 to 2000 oligonucleotides, or from 5 to 2000, or from 10 to 2000, or from 25 or 50 to 80, 91, 100, 200, or 500 or 1000 oligonucleotides. In this preferred embodiment, each microchip includes at least 2, 3, 4, 5, 6, 7, 8, 9, 10, 12, 15, 20, 25, 30, 40 or 50, or at least 70, 80, 90 or 100 variant-containing oligonucleotides of the present invention each containing one different nucleotide variant selected from those in Tables 1-2, or the complement thereof. In specific embodiments, each of the variant-containing oligonucleotides comprises a contiguous span of at least 12, 15, 17, 18, 19, 20, 21, 22, 23, 24, 25, 26, 27, 28, 29, 30, 40, 50, 70 or 100 nucleotide residues of any one of SEQ ID NOs:1-192, and each contains one different nucleotide variant of those in Tables 1-2, or the complement thereof. In preferred embodiments, each variant-containing oligonucleotide has a contiguous span of from about 17, 18, 19, 20, 21, 22, 23 or 25 to about 30, 40 or 50, preferably from about 21 to about 30, 40, 50 or 60 nucleotide residues, of any one of SEQ ID NOs:1-192, containing one nucleotide variant selected from those in Tables 1-2, or the complement thereof.

The DNA microchip can be useful in detecting predisposition to BRCA2-associated cancer, particularly breast and ovarian cancers, diagnosing BRCA2-associated cancer, particularly breast and ovarian cancers, and selecting treatment or prevention regimens.

4. Genotyping

The present invention also provides a method for genotyping by determining whether an individual has one or more of the nucleotide variants or amino acid variants of the present invention. The individual to be genotyped can be normal or without cancer. The individual can genotyped can be one diagnosed of cancer, particularly breast or ovarian cancer. Genotyping or mutation detection in individuals diagnosed of cancer is useful in determining whether the cancer is BRCA2-associated hereditary cancer.

Similarly, a method for haplotyping is also provided, i.e., to identify LD variants. Haplotyping can be done by any methods known in the art. For example, only one copy of a genomic region can be isolated from an individual and the nucleotide at each of the variant positions is determined. Alternatively, an allele specific PCR or a similar method can be used to amplify only one copy of a genomic region of interest in an individual, and the nucleotide variants at the variant positions of the present invention are determined. The Clark method known in the art can also be employed for haplotyping. A high throughput molecular haplotyping method is also disclosed in Tost et al., *Nucleic Acids Res.*, 30(19):e96 (2002), which is incorporated herein by reference.

Thus, additional variant(s) (LD variants) that are in linkage disequilibrium with the nucleotide variants and/or haplotypes of the present invention can be identified by a haplotyping method known in the art, as will be apparent to a skilled artisan in the field of genetics and haplotying. The additional variants that are in linkage disequilibrium with a nucleotide variant in Tables 1-2 can also be useful in the various applications as described below.

For purposes of genotyping and haplotyping, both genomic DNA and mRNA/cDNA can be used, and both are herein referred to generically as "gene."

Numerous techniques for detecting nucleotide variants are known in the art and can all be used for the method of this invention. The techniques can be protein-based or DNA-based. In either case, the techniques used must be sufficiently sensitive so as to accurately detect the small nucleotide or amino acid variations. Very often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977).

In a DNA-based detection method, target DNA sample, i.e., a sample containing a genomic region of interest, or the corresponding cDNA or mRNA must be obtained from the individual to be tested. Any tissue or cell sample containing the relevant genomic DNA, mRNA, or cDNA or a portion thereof can be used. For this purpose, a tissue sample containing cell nucleus and thus genomic DNA can be obtained from the individual. Blood samples can also be useful except that only white blood cells and other lymphocytes have cell nucleus, while red blood cells are anucleate and contain only mRNA. Nevertheless, mRNA is also useful as it can be analyzed for the presence of nucleotide variants in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence or absence of a particular nucleotide variant, one technique is simply sequencing the target genomic DNA or cDNA, particularly the region encompassing the nucleotide variant locus to be detected. Various sequencing techniques are generally known and widely used in the art including the Sanger method and Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and thus can also be used in the present invention. See Nordstrom et al., *Biotechnol. Appl. Biochem.*, 31(2):107-112 (2000); Ahmadian et al., *Anal. Biochem.*, 280: 103-110 (2000).

Alternatively, the restriction fragment length polymorphism (RFLP) and AFLP method may also prove to be useful techniques. In particular, if a nucleotide variant in the target nucleic acid region results in the elimination or creation of a restriction enzyme recognition site, then digestion of the target DNA with that particular restriction enzyme will generate an altered restriction fragment length pattern. Thus, a detected RFLP or AFLP will indicate the presence of a particular nucleotide variant.

Another useful approach is the single-stranded conformation polymorphism assay (SSCA), which is based on the altered mobility of a single-stranded target DNA spanning the nucleotide variant of interest. A single nucleotide change in the target sequence can result in different intramolecular base pairing pattern, and thus different secondary structure of the single-stranded DNA, which can be detected in a non-denaturing gel. See Orita et al., *Proc. Natl. Acad. Sci. USA*, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., *Biotechniques*, 5:1016-24 (1999); Sheffield et al., *Am. J. Hum, Genet.*, 49:699-706 (1991); Wartell et al., *Nucleic Acids Res.*, 18:2699-2705 (1990); and Sheffield et al., *Proc. Natl. Acad. Sci. USA*, 86:232-236 (1989). In addition, the double-strand conformation analysis (DSCA) can also be useful in the present invention. See Arguello et al., *Nat. Genet.*, 18:192-194 (1998).

The presence or absence of a nucleotide variant at a particular locus in a genomic region of an individual can also be detected using the amplification refractory mutation system (ARMS) technique. See e.g., European Patent No. 0,332,435; Newton et al., *Nucleic Acids Res.*, 17:2503-2515 (1989); Fox et al., *Br. J. Cancer*, 77:1267-1274 (1998); Robertson et al., *Eur. Respir. J.*, 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., *Clin. Chem.* 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., *Genomics*, 8:684-692 (1990); Shumaker et al., *Hum. Mutat.*, 7:346-354 (1996); Chen et al., *Genome Res.*, 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science*, 241:1077-1080 (1988); Chen et al, *Genome Res.*, 8:549-556 (1998); Iannone et al., *Cytometry*, 39:131-140 (2000). Thus, for example, to detect a single-nucleotide mutation at a particular locus in a genomic region, two oligonucleotides can be synthesized, one having the genomic sequence just 5' upstream from the locus with its 3' end nucleotide being identical to the nucleotide in the variant locus, the other having a nucleotide sequence matching the genomic sequence immediately 3' downstream from the variant locus. The oligonucleotides can be labeled for the purpose of detection. Upon hybridizing to the target nucleic acid under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., *Proc. Natl. Acad. Sci. USA,* 80:278-282 (1983); Saiki et al, *Proc. Natl. Acad. Sci. USA,* 86:6230-6234 (1989). Oligonucleotide probes (allele-specific) hybridizing specifically to an allele having a particular nucleotide variant at a particular locus but not to other alleles can be designed by methods known in the art. The probes can have a length of, e.g., from 10 to about 50 nucleotide bases. The target DNA and the oligonucleotide probe can be contacted with each other under conditions sufficiently stringent such that the nucleotide variant can be distinguished from the alternative variant/allele at the same locus based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular nucleotide variant.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, *Human Genetics,* 42:726 (1988). Alternatively, in a RNase protection assay, a RNA probe can be prepared spanning the nucleotide variant site to be detected and having a detection marker. See Giunta et al., *Diagn. Mol. Path.,* 5:265-270 (1996); Finkelstein et al., *Genomics,* 7:167-172 (1990); Kinszler et al., *Science* 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., *Nucleic Acids Res.,* 25:3377-3378 (1997).

In the mutS assay, a probe can be prepared matching the human nucleic acid sequence surrounding the locus at which the presence or absence of a nucleotide variant is to be detected, except that a predetermined nucleotide is used at the variant locus. Upon annealing the probe to the target DNA to form a duplex, the *E. coli* mutS protein is contacted with the duplex. Since the mutS protein binds only to heteroduplex sequences containing a nucleotide mismatch, the binding of the mutS protein will be indicative of the presence of a mutation. See Modrich et al., *Ann. Rev. Genet.,* 25:229-253 (1991).

A great variety of improvements and variations have been developed in the art on the basis of the above-described basic techniques, and can all be useful in detecting mutations or nucleotide variants in the present invention. For example, the "sunrise probes" or "molecular beacons" utilize the fluorescence resonance energy transfer (FRET) property and give rise to high sensitivity. See Wolf et al., *Proc. Nat. Acad. Sci. USA,* 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., *Nucleic Acids Res.,* 25:2516-2521 (1997); Rychlik et al., *Nucleic Acids Res.,* 17:8543-8551 (1989); Sharkey et al., *Bio/Technology* 12:506-509 (1994); Tyagi et al., *Nat. Biotechnol.,* 14:303-308 (1996); Tyagi et al., *Nat. Biotechnol.,* 16:49-53 (1998). The homo-tag assisted non-dimer system (HANDS) can be used in combination with the molecular beacon methods to suppress primer-dimer accumulation. See Brownie et al., *Nucleic Acids Res.,* 25:3235-3241 (1997).

Dye-labeled oligonucleotide ligation assay is a FRET-based method, which combines the OLA assay and PCR. See Chen et al., *Genome Res.* 8:549-556 (1998). TaqMan is another FRET-based method for detecting nucleotide variants. A TaqMan probe can be oligonucleotides designed to have the nucleotide sequence of the human nucleic acid spanning the variant locus of interest and to differentially hybridize with different alleles. The two ends of the probe are labeled with a quenching fluorophore and a reporter fluorophore, respectively. The TaqMan probe is incorporated into a PCR reaction for the amplification of a target nucleic acid region containing the locus of interest using Taq polymerase. As Taq polymerase exhibits 5'-3' exonuclease activity but has no 3'-5' exonuclease activity, if the TaqMan probe is annealed to the target DNA template, the 5'-end of the TaqMan probe will be degraded by Taq polymerase during the PCR reaction thus separating the reporting fluorophore from the quenching fluorophore and releasing fluorescence signals. See Holland et al., *Proc. Natl. Acad. Sci. USA,* 88:7276-7280 (1991); Kalinina et al., *Nucleic Acids Res.,* 25:1999-2004 (1997); Whitcombe et al., *Clin. Chem.,* 44:918-923 (1998).

In addition, the detection in the present invention can also employ a chemiluminescence-based technique. For example, an oligonucleotide probe can be designed to hybridize to either the wild-type or a variant locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., *Nucleic Acids Res.,* 24:4998-5003 (1996).

The detection of genetic variation in accordance with the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., *Electrophoresis,* 20:1171-1176 (1999).

Another useful technique that is gaining increased popularity is mass spectrometry. See Graber et al., *Curr. Opin. Biotechnol.,* 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., *Nat. Med.,* 3:360-362 (1997).

In addition, the microchip or microarray technologies are also applicable to the detection method of the present invention as will be apparent to a skilled artisan in view of this disclosure. For example, to genotype an individual, genomic DNA isolated from the individual can be prepared and hybridized to a DNA microchip of the present invention as described above in Section 3, and the genotypes at a plurality of loci can be determined.

As is apparent from the above survey of the suitable detection techniques, it may or may not be necessary to amplify the target DNA, i.e., the genomic region of interest, or the corresponding cDNA or mRNA to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual*, $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.*, 34:901-907 (1996); Collins et al., *Nucleic Acids Res.*, 25:2979-2984 (1997); Horn et al., *Nucleic Acids Res.*, 25:4835-4841 (1997); Horn et al., *Nucleic Acids Res.*, 25:4842-4849 (1997); Nilsen et al., *J. Theor. Biol.*, 187:273-284 (1997).

In yet another technique for detecting single nucleotide variations, the Invader® assay utilizes a novel linear signal amplification technology that improves upon the long turn-around times required of the typical PCR DNA sequenced-based analysis. See Cooksey et al., *Antimicrobial Agents and Chemotherapy* 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader® system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., *Nat. Biotechnol.*, 17:292-296 (1999).

The rolling circle method is another method that avoids exponential amplification. Lizardi et al., *Nature Genetics*, 19:225-232 (1998) (which is incorporated herein by reference). For example, Sniper™, a commercial embodiment of this method, is a sensitive, high-throughput SNP scoring system designed for the accurate fluorescent detection of specific variants. For each nucleotide variant, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, *Life Science News* 6, 2000, *Amersham Pharmacia Biotech* (2000).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., *Anal. Chem.*, 69:4703-4707 (1997). The fluorescence correlation spectroscopy is based on the spatio-temporal correlations among fluctuating light signals and trapping single molecules in an electric field. See Eigen et al., *Proc. Natl. Acad. Sci. USA*, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.*, 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a nucleotide variant in a genomic region of a particular individual should be apparent to a skilled artisan apprised of this disclosure.

Protein-based detection techniques may also prove to be useful, especially when the nucleotide variant causes amino acid substitutions or deletions or insertions or frameshift that affect the protein primary, secondary or tertiary structure. To detect the amino acid variations, protein sequencing techniques may be used. For example, a protein or fragment thereof can be synthesized by recombinant expression using an encoding cDNA fragment isolated from an individual to be tested. Preferably, a cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., *Anal. Chem.*, 72:757-763 (2000).

Other useful protein-based detection techniques include immunoaffinity assays based on antibodies selectively immunoreactive with mutant proteins according to the present invention. The method for producing such antibodies is described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

Accordingly, the presence or absence of a nucleotide variant or amino acid variant in an individual can be determined using any of the detection methods described above.

The present invention also provides a kit for genotyping, i.e., determining the presence or absence of one or more of the nucleotide or amino acid variants of present invention in the genomic DNA, or cDNA or mRNA in a sample obtained from a patient. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting nucleotide or amino acid variants discovered in accordance with the present invention using the above-discussed detection techniques.

In one embodiment, the detection kit includes one or more oligonucleotides useful in detecting one or more of the nucleotide variants in Tables 1-2, or an LD variant thereof. The oligonucleotides can be in one or more compartments or containers in the kit. In a preferred embodiment, the kit has a plurality of from 2 to 2000 oligonucleotides, or from 5 to 2000, or from 10 to 2000, or from 25 or 50 to 500, 1000, 1500 or 2000 oligonucleotides. In this preferred embodiment, each kit includes at least 2, 3, 4, 5, 6, 7, 8, 9, 10, 12, 15, 20, 25, 30, 40 or 50, or at least 70, 80, 90 or 100 variant-containing oligonucleotides of the present invention each containing one different nucleotide variant selected from those in Tables 1-2, or the complement thereof. In specific embodiments, each of the variant-containing oligonucleotides comprises a contiguous span of at least 12, 15, 17, 18, 19, 20, 21, 22, 23, 24, 25, 26, 27, 28, 29, 30, 40, 50, 70 or 100 nucleotide residues of any one of SEQ ID NOs:1-192, and each contains one different nucleotide variant of those in Tables 1-2, or the complement thereof. In preferred embodiments, each variant-containing oligonucleotide has a contiguous span of from about 17, 18, 19, 20, 21, 22, 23 or 25 to about 30, 40 or 50, preferably from about 21 to about 30, 40, 50 or 60 nucleotide residues, of any one of SEQ ID NOs:1-192, containing one nucleotide variant selected from those in Tables 1-2, or the complement thereof.

In the kit of the present invention having oligonucleotides, the oligonucleotides can be affixed to a solid support, e.g., incorporated in a microchip or microarray included in the kit. In other words, microchips and microarrays according to the present invention described above in Section 3 can be included in the kit.

Preferably, the oligonucleotides are allele-specific, i.e., are designed such that they hybridize only to a human nucleic acid of a particular allele, i.e., containing a particular nucleotide variant (versus the alternative variant at the same locus) discovered in accordance with the present invention, under stringent conditions. Thus, the oligonucleotides can be used in mutation-detecting techniques such as allele-specific oligonucleotides (ASO), allele-specific PCR, TaqMan, chemiluminescence-based techniques, molecular beacons, and improvements or derivatives thereof, e.g., microchip technologies. The oligonucleotides in this embodiment preferably have a nucleotide sequence that matches a nucleotide sequence of a variant allele containing a nucleotide variant to be detected. The length of the oligonucleotides in accordance with this embodiment of the invention can vary depending on its nucleotide sequence and the hybridization conditions employed in the detection procedure. Preferably, the oligonucleotides contain from about 10 nucleotides to about 100 nucleotides, more preferably from about 15 to about 75 nucleotides, e.g., a contiguous span of 18, 19, 20, 21, 22, 23, 24 or 25 to 21, 22, 23, 24, 26, 27, 28, 29 or 30 nucleotide residues of a nucleic acid one or more of the residues being a nucleotide variant of the present invention, i.e., selected from Tables 1-2 or an LD variant thereof. Under some conditions, a length of 18 to 30 may be optimum. In any event, the oligonucleotides should be designed such that it can be used in distinguishing one nucleotide variant from another at a particular locus under predetermined stringent hybridization conditions. Preferably, a nucleotide variant is located at the center or within one (1) nucleotide of the center of the oligonucleotides, or at the 3' or 5' end of the oligonucleotides. The hybridization of an oligonucleotide with a nucleic acid and the optimization of the length and hybridization conditions should be apparent to a person of skill in the art. See generally, Sambrook et al., *Molecular Cloning: A Laboratory Manual*, 2$^{nd}$ ed., Cold Spring Harbor Laboratory, Cold Spring Harbor, N.Y., 1989. Notably, the oligonucleotides in accordance with this embodiment are also useful in mismatch-based detection techniques described above, such as electrophoretic mobility shift assay, RNase protection assay, mutS assay, etc.

In another embodiment of this invention, the kit includes one or more oligonucleotides suitable for use in detecting techniques such as ARMS, oligonucleotide ligation assay (OLA), and the like. The oligonucleotides in this embodiment include a human nucleic acid sequence of about 10 to about 100 nucleotides, preferably from about 15 to about 75 nucleotides, e.g., contiguous span of 18, 19, 20, 21, 22, 23, 24 or 25 to 21, 22, 23, 24, 26, 27, 28, 29 or 30 nucleotide residues immediately 5' upstream from the nucleotide variant to be analyzed. The 3' end nucleotide in such oligonucleotides is a nucleotide variant in accordance with this invention.

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.*, 14:6115-6128 (1986); Nguyen et al., *Biotechniques*, 13:116-123 (1992); Rigby et al., *J. Mol. Biol.*, 113:237-251 (1977). Alternatively, the oligonucleotides included in the kit are not labeled, and instead, one or more markers are provided in the kit so that users may label the oligonucleotides at the time of use.

In another embodiment of the invention, the detection kit contains one or more antibodies selectively immunoreactive with certain protein variants containing specific amino acid variants discovered in the present invention. Methods for producing and using such antibodies have been described above in detail.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit preferably includes instructions on using the kit for detecting nucleotide variants in human samples.

5. Use of Genotyping in Diagnosis Applications

As indicated above, specific alleles of the variants presented in Tables 1-2 have been found in the human BRCA2 gene. Thus, the deleterious variants are useful in predicting an enhanced risk or a predisposition to BRCA2-associated cancer, particularly breast and ovarian cancers in an individual.

The non-deleterious polymorphisms are also useful in that once they are detected in an individual's BRCA2 gene in the absence of any other deleterious mutations, then the individual is BRCA2 wild-type. That is, the individual does not have any BRCA2 mutation, and does not have a BRCA2-associated predisposition to cancer.

Thus, in one aspect, the present invention encompasses a method for predicting or detecting susceptibility to BRCA2-associated cancer, particularly breast and ovarian cancers in an individual, which comprises the step of genotyping the individual to determine the individual's genotypes at one or more of the loci identified in the present invention, or another locus at which the genotype is in linkage disequilibrium with one of the variants of the present invention. In specific embodiments, the method for detecting a predisposition or an increased likelihood of developing BRCA2-associated cancer, particularly breast and ovarian cancers in an individual comprises determining the presence or absence of one or more nucleotide variants as disclosed in Table 1 that are associated with BRCA2-associated cancer, particularly breast and ovarian cancers, or one or more LD variants thereof. Thus, if one or more of the nucleotide variants in Table 1 associated with BRCA2-associated cancer, particularly breast and ovarian cancers are detected, or one or more LD variants thereof are detected in the individual, then it can be reasonably predicted that the individual is at an increased risk of developing BRCA2-associated cancer, particularly breast and ovarian cancers. If a variant in Table 2 is detected, then if the patient has no other deleterious BRCA2 mutations, then the patient does not have a BRCA2-conferred predisposition to BRCA2-associated cancer, particularly breast and ovarian cancers.

In one embodiment, the method of detecting a predisposition is applied in organ or tissue transplants. For example, before transplantation, the method of the present invention is applied to determine if the donor has a predisposition to BRCA2-associated cancer, particularly breast and ovarian cancers.

In another aspect, the present invention encompasses a method for diagnosing BRCA2-associated cancer, particularly breast and ovarian cancers in an individual or assessing the likelihood that an individual having BRCA2-associated cancer, particularly breast and ovarian cancers, which comprises the step of genotyping the individual to determine the individual's genotypes at one or more of the loci identified in the present invention, or another locus at which the genotype is in linkage disequilibrium with one of the variants of the present invention. In specific embodiments, the method for diagnosing BRCA2-associated cancer, particularly breast and ovarian cancers in an individual or assessing the likelihood that an individual having BRCA2-associated cancer, particularly breast and ovarian cancers, comprises determining the presence or absence of one or more nucleotide variants as disclosed in Table 1 that are associated with BRCA2-associated cancer, particularly breast and ovarian cancers, or one or more LD variants thereof. Thus, if one or more of the nucleotide variants in Table 1 associated with BRCA2-associated cancer, particularly breast and ovarian cancers are detected, or one or more LD variants thereof are detected in the individual, then it can be reasonably predicted that the individual has BRCA2-associated cancer, particularly breast and ovarian cancers, or that there is an increased likelihood that the individual has BRCA2-associated cancer, particularly breast and ovarian cancers.

If a variant in Table 2 is detected, and if the patient has no other deleterious BRCA2 mutations, then the patient does not have an increased likelihood of having a BRCA2-associated cancer, particularly breast and ovarian cancers.

In yet another aspect, the present invention encompasses a method for identifying individuals who might benefit from prophylactic treatment for BRCA2-associated cancer, particularly breast and ovarian cancers, which comprises the step of genotyping the individual to determine the individual's genotypes at one or more of the loci identified in the present invention, or another locus at which the genotype is in linkage disequilibrium with one of the variants of the present invention. In specific embodiments, the method comprises determining in an individual the presence or absence of one or more nucleotide variants as disclosed in Table 1 that are associated with BRCA2-associated cancer, particularly breast and ovarian cancers, or one or more LD variants thereof. Thus, if one or more of the nucleotide variants in Table 1 associated with BRCA2-associated cancer, particularly breast and ovarian cancers are detected, or one or more LD variants thereof are detected in the individual, then it can be reasonably predicted that the individual might benefit from prophylactic treatment for BRCA2-associated cancer, particularly breast and ovarian cancers. If a variant in Table 2 is detected, and if the patient has no other deleterious BRCA2 mutations, then the patient does not have a BRCA2-conferred predisposition to BRCA2-associated cancer, particularly breast and ovarian cancers.

In yet another aspect, the present invention encompasses a method for identifying candidate individuals for a clinical trial or research testing, which comprises the step of genotyping the individual to determine the individual's genotypes at one or more of the loci identified in the present invention, or another locus at which the genotype is in linkage disequilibrium with one of the variants of the present invention. In specific embodiments, the method comprises determining in an individual the presence or absence of one or more nucleotide variants as disclosed in Table 1 that are associated with BRCA2-associated cancer, particularly breast and ovarian cancers, or one or more LD variants thereof. Thus, if one or more of the nucleotide variants in Table 1 associated with BRCA2-associated cancer, particularly breast and ovarian cancers are detected, or one or more LD variants thereof are detected in the individual, then this fact is considered in deciding whether to include in the individual in the clinical trial or research testing. Thus, in one embodiment, a method is provided comprising determining in an individual the presence or absence of one or more nucleotide variants as disclosed in Table 1 that are associated with BRCA2-associated cancer, particularly breast and ovarian cancers, or one or more LD variants thereof, and including or excluding the individual when the individual in a particular clinical trial or research testing. The clinical trials or tests can be a trial or test for a diagnostic product or method, or a testing for a therapeutic or prophylactic product or method, or a test for researching diseases or disorders that are typically seen associated with BRCA2-associated cancer, particularly breast and ovarian cancers, or more prevalent in BRCA2-associated cancer, particularly breast and ovarian cancers patients.

In yet another aspect, the present invention encompasses a method for determining the drug response of an individual under a medical treatment or prevention, e.g., administered with a therapeutic or prophylactic drug or another substance. The method comprises placing the individual under the medical treatment or prevention, genotyping the individual to determine the individual's genotypes at one or more of the loci identified in the present invention, or another locus at which the genotype is in linkage disequilibrium with one of the variants of the present invention, and determining the effect of the medical treatment or prevention on the individual, and optionally comparing or correlating the genotype and the effect. In specific embodiments, the method comprises determining in an individual the presence or absence of one or more nucleotide variants as disclosed in Table 1 that are associated with BRCA2-associated cancer, particularly breast and ovarian cancers, or one or more LD variants thereof, determining the effect of the treatment or prevention regimen the individual is undergoing, and optionally comparing or correlating the genotype and the effect. In other specific embodiments, the method is used for determining the drug response of an individual under a treatment or prevention for BRCA2-associated cancer, particularly breast and ovarian cancers or a disease or disorder typically associated with or prevalent in BRCA2-associated cancer, particularly breast and ovarian cancers patients. The method comprises placing the individual under a treatment or prevention for BRCA2-associated cancer, particularly breast and ovarian cancers, genotyping the individual to determine the individual's genotypes at one or more of the loci identified in the present invention, or another locus at which the genotype is in linkage disequilibrium with one of the variants of the present invention, and determining the effect of the treatment or prevention regimen the individual is undergoing, and optionally comparing or correlating the genotype and the effect. If a variant in Table 2 is detected, then if the patient has no other deleterious BRCA2 mutations, then the patient does not have a BRCA2-conferred predisposition to BRCA2-associated cancer, particularly breast and ovarian cancers.

In yet another aspect of the present invention, a method is provided for treating a patient with a therapeutic or prophylactic treatment regimen, or for determining whether a therapeutic or prophylactic treatment regimen should be used on an individual, comprising determining in an individual the presence or absence of one or more nucleotide variants as disclosed in Table 1 that are associated with BRCA2-associated cancer, particularly breast and ovarian cancers, or one or more LD variants thereof, and correlating the genotype with a therapeutic or prophylactic treatment regimen. In one embodiment, the method comprises determining in an individual the presence or absence of one or more nucleotide variants as disclosed in Table 1 that are associated with BRCA2-associated cancer, particularly breast and ovarian cancers, or one or more LD variants thereof, and correlating the genotype with a therapeutic or prophylactic treatment regimen, wherein when the individual has one or more nucleotide variants as disclosed in Table 1 that are associated with BRCA2-associated cancer, particularly breast and ovarian cancers, or one or more LD variants thereof, then the therapeutic or prophylactic treatment regimen is used. In another embodiment, the method comprises determining in an individual the presence or absence of one or more nucleotide variants as disclosed in Table 1 that are associated with BRCA2-associated cancer, particularly breast and ovarian cancers, or one or more LD variants thereof, and correlating the genotype with a therapeutic or prophylactic treatment regimen, wherein when the individual has one or more nucleotide variants as disclosed in Table 1 that are associated with BRCA2-associated cancer, particularly breast and ovarian cancers, or one or more LD variants thereof, then the therapeutic or prophylactic treatment regimen is not used.

Typically, once genotype at a variant locus or the presence or absence of a particular nucleotide variant or an amino acid variant resulting from a nucleotide variant of the present invention is determined or the disease diagnosis or prognosis correlating to the genotype is made, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to the presence or absence of a particular nucleotide variant of the present invention in the individual tested can be embodied in descriptive statements, diagrams, photographs, charts, images or any other visual forms. For example, images of gel electrophoresis of PCR products can be used in explaining the results. Diagrams showing where a variant occurs in an individual genome are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of a nucleotide variant or amino acid variant of the present invention in the individual tested can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present invention also encompasses a method for producing a transmittable form of information on a genotype of an individual. The method comprises the steps of (1) determining the presence or absence of a nucleotide variant according to the present invention in the genome of the individual; and (2) embodying the result of the determining step in a transmittable form. The transmittable form is the product of the production method.

In some embodiments of the above aspects, whenever appropriate, the individual identified as having a predisposition to, or having, BRCA2-associated cancer, particularly breast and ovarian cancers, can be treated with a suitable treatment regimen to treat or alleviate the symptoms of, or delaying the onset of BRCA2-associated cancer, particularly breast and ovarian cancers. Any treatment or prophylactic regimens known in the art presently or in the future can all be used. Thus, the present invention further provides a method for preventing, slowing the onset, and/or treating cancer in an individual. This method can include, for example, (i) detecting, in an individual, the presence of a genetic variant in the BRCA2 gene in Tables 1-2; and (ii) determining a therapy to treat, prevent, or slow the progression of cancer in the individual based on the presence or absence of one or more of the genetic variants. The method may further include administering a therapeutic to treat, delay the onset of, or slow the progression of, cancer to the individual.

Detection of a mutation in one or more of the BRCA2 mutations in an individual is useful in determining a therapy to treat, prevent, or slow the progression of cancer, especially breast cancer and ovarian cancer. Treatments useful in the prevention or delay the onset of BRCA2-associated cancers include, but are not limited to, increased surveillance for cancer and preventative treatments such as prophylactic surgeries and/or drug therapy.

In one aspect, a suitable treatment may include increased surveillance of an individual to detect the development of breast cancer using mammography and/or other imaging devices. Surveillance screening for the detection of breast cancer in an individual having a mutation of the present invention can be performed in a number of ways. For example, the currently recommended breast cancer surveillance in BRCA2 carriers includes breast self-examination, bi-annual clinical examinations and annual screens using mammography. See Brekelmans, et al., *J. Clin. Oncol.*, 19:924-930 (2001).

A mammogram is a low dose x-ray of the breast commonly used as a screening tool to detect breast cancer in women. Specifically, the breast is exposed to radiation to produce an image of the internal tissue which is typically recorded on film. The image is formed as the x-rays pass through or are absorbed by breast tissue. See, Gizvold, J. J., *Mayo Clin. Proc.*, 65(1):56-66 (1990). To overcome limitations of the film-screen mammography technique, the digital or full-field digital mammography (FFDM) may be used. FFDM replaces x-ray film with solid-state detectors which convert x-rays to electrical signals to produce an image. See Kuzmiak, et al., *Med. Phys.*, 32(10):3144-50 (2005).

Another method used to detect carcinomas is magnetic resonance imaging (MRI). This technique utilizes a powerful magnetic field and radio waves to create and image of the breast tissue. Subsequent to positioning the individual, a radio wave is sequentially turned on and off. An image is recorded from energy reflected back (or echoed) by the body. See Kacher, et al., *Radiol. Clin. North Am.*, 42(5):947-962 (2004). The CP BREAST COIL by SIEMENS is a recent advance is MRI for breast cancer which allows for bilateral breast imaging and increased tissue differentiation. A contrast media such as Gadolinium DPTA may be used to increase the observable difference in dense tissue, such as that caused by scarring, and carcinoma. See Stack, et al., *Radiology*, 174: 491-494 (1990). MRI provides several advantages over other means of imagining techniques including improved staging and treatment planning, increased evaluation of augmented breasts, better detection and improved screening. See Goscin, et al., *Cancer Control.*, 8(5):399-406 (2001).

Positron emission tomography (PET) imaging can be used in obtaining both anatomical and metabolic information. A positron-emitting radionuclide is injected into the body of the individual being tested. Examples of suitable radionuclides are 2-[F18]fluoro-2-deoxy-D-glucose (FDG), Sestamibi Tc99m, Tl 201 and Cyanocobalamin Co 57, to name a few. See Weir, et al., *Breast J.*, 11(3):204-209 (2005); Alonso, et al., *Anticancer Res.*, 17(3B):1661-5 (1997). The radionuclides accumulate in varying levels according to tissue type. Subsequently, emission of positrons from the accumulated radionuclides can be recorded by PET scanners to create an image. This technique is particularly useful in characterizing indeterminate palpable masses and detecting auxillary masses. See Benard, et al., *Breast Cancer Res.*, 7(4):153-162 (2005).

Ultrasound (US) or sonography is a technique utilizing high-frequency sound waves to form an image of internal tissue. Although this method has traditionally been used to evaluate tumor abnormal breast tissue discovered during physical examination or mammography, its use as first means of detection in high risk individuals is increasing. The predominant use of US is in the differentiation of cystic and solid masses in the breast. Recently US has been demonstrated as an accurate means of classifying solid masses in the breast as benign or malignant. See Stavros, et al., *Radiology*, 196:123-134 (1995).

Mammary ductoscope is yet another technique that may be used to monitor an individual for development of breast cancer. This technique allows for direct visualization of the milk duct lumen and lobule, where most breast carcinomas and pre-cancers originate. A fiberoptic micro-endoscope (such as MASTASCOPE from Lifeline Techonlogies) is inserted through the ductal opening of the breast. Magnified images of the mammary ductal epithelium are conveyed to and viewed on a monitor. The endoscopes may be a microcatherter further allowing for ductal lavage testing in combination with ductoscope imaging. See Mokbel, et al., *Eur. J. Sur. Oncol.*, 31(1):3-8 (2005).

Another technique useful in the surveillance of individuals having a predisposition to BRCA2 associated cancers is the ductal lavage. Cancerous and pre-cancerous cells are identified by collecting and examining cells from the milk ducts. The purpose is to obtain cells surrounding those undergoing malignant transformation, thereby providing a means for detection prior to development of a discernable mass. See Dua, et al., *J. Clin. Oncol.*, 24(7):1209-16 (2006).

Techniques such as electrical impedance scanning and light scanning (or transillumination) are advantageous in the breast cancer surveillance as they provide a less invasive and more cost effective means of detecting cancerous and precancerous cells without the use of radiation. Different tissue types have different electrical impedance levels. Cancerous breast tissue has much lower electrical impedance than healthy tissue, thus, electrical impedance scanning is yet another means of breast cancer surveillance. A small electrical current is passed through the body using an electrode. As the current travels through the body, an electrical impedance scanning device, such as the T-SCAN 2000 from TransScan Medical, Inc., is used to measure the amount of current carried by different tissues. A tissue having lower electrical impedance (i.e. a better conductor of electric current) such as cancerous breast tissue appears as a bright white spot on the computer generated image. See Hope, et al., *Breast Cancer Res.*, 6(2):69-74 (2004).

The premise of the light scanning technique is the light absorption characteristics of the breast tissue. Because cancerous tissue has an increased blood supply, it absorbs light near the infrared range as opposed to normal tissue which absorbs light near the blue range. See *Health Technol. Assess Rep.*, 2(10):1-7 (1988); U.S. Pat. No. 4,945,239.

In another aspect, the treatment includes surveillance of ovarian cancer in an individual having a genetic variation in one or more of the genetic variants of the present invention. Ovarian cancer surveillance may be performed in a number of ways known in the art. For example, the surveillance for ovarian cancer may be performed by transvaginal ultrasound (TVUS). As described above, an image is created using ultrasound by measuring the reflection of high-frequency sound waves from tissues. The TVUS may be used to detect ovarian cancer in ovaries, uterus, cervix and fallopian tubes. See Modugno, et al., *Gynecol. Oncol.*, 91(1):15-31 (2003).

Another means of conducting ovarian cancer surveillance in an individual is the determination of cancer antigen-125 (CA-125) levels in the blood. CA-125 is a protein found to be elevated in epithelial ovarian cancer. Elevated CA-125 levels have preceded clinical detection of recurring ovarian cancer by at least 3 months in most cases. See Bast, et al., *Int. J. Biol. Markers*, 13(4):179-187 (1998).

In yet another aspect, the method is useful in determining a preventive treatment for an individual having a genetic variation in one or more of the BRCA2 variants of the present invention prior to the onset of cancer. For example, the preventive treatment may include drug therapy involving chemotherapeutics, hormone replacement therapy and/or hormone therapy. In a specific example, a preventative treatment may include an estrogen receptor modulator or an aromatase inhibitor useful to prevent or slow the development of cancer.

Estrogen is a well-known factor in the stimulation of breast carcinoma. Evidence shows that there may be some interaction between BRCA2 and estrogen. See Noruzinia, et al., *Cancer,* 104(8):1567-74 (2005). Furthermore, it has recently been shown that BRCA2 associated cancers may be estrogen sensitive. See Bramley, et al., *Br. J. Cancer.,* 94(7):1021-8 (2006)

Thus, a drug that blocks or modifies the effects of estrogen may be used to prevent the development of cancer. For example, selective estrogen receptor modulators (SERMs) such as tamoxifen (NOLVADEX®), raloxifene (EVISTA®), lasofoxifene and/or letrozole (FEMERA®) may be administered to an individual having an increased risk of breast cancer. SERMs are anti-estrogen compounds that act as estrogen agonists and antagonists by interacting with estrogen receptors. Anti-estrogen therapy has been shown to reduce the risk of cancer recurrence in BRCA2 mutation carriers. See Bramley, et al., *Br. J. Cancer.,* 94(7):1021-8 (2006).

Local estrogen synthesis through the activity of aromatase has also been implicated in the stimulation of cancer growth. Drugs such as letrozole, anastrozole, and vorozole (nonsteroidal, type II) and exemestane (steroidal, type I), function by inhibiting aromatase activity, thereby blocking production of cancer causing estrogen. See Goss, et al., *J. Clin. Oncol.,* 19(3):884-891 (2001). Aromatase inhibitors may be used as a primary treatment or in combination with other drugs such as SERMs. Recently, aromatase inhibitors have been shown to be more effective and less toxic than tamoxifen in advanced disease and in the neoadjuvant and adjuvant setting. See Goss, et al., *Best. Pract. Res. Clin. Endocrinol. Metab.,* 18(1): 113-30 (2004).

Other methods of preventing and treating individuals may include hormones including administering birth control pills such as progesterone antagonists (e.g., RU-486), hormone replacement therapy and/or hormone therapy.

In another example, preventative therapy may include prophylactic surgery such as preventative mastectomy (i.e. prophylactic or risk-reducing mastectomy). Preventative mastectomy is the removal of healthy breast tissue performed to prevent or reduce the risk of breast cancer in an individual having a mutation in the BRCA2 gene. Removal or both breasts has been shown to reduce the risk of breast cancer in women by 90-95%. See Ribbeck, et al., *J. Clin. Oncol.,* 22:1055-1062 (2004).

Prophylactic surgery to prevent the development of cancers associated with BRCA2 mutation may also involve surgical removal of the ovaries (i.e. oophorectomy), fallopian tubes and/or hysterectomy. Oophorectomy involves the removal of either one or both ovaries to end secretion of estrogen, which simulates cancer development. This procedure is especially effective in pre-menopausal. To preserve fertility in younger women and/or those with a lesser risk of developing cancer, it may be preferable to perform a fertility-saving or fertility sparing surgery such as a partial or unilateral oopherectomy. See Ribbeck, et al., *N. Engl. J. Med.,* 346:1616-1622 (2002).

A bilateral salpingo-oophorectomy, removal of both the ovaries and may also be performed to decrease the risk of BRCA2 associated cancers. See Kauff, et al., *N. Engl. J. Med.,* 346:1609-1615 (2002).

In another aspect, the treatment may be used to slow cancer progression in an individual diagnosed with cancer and having a genetic variant of the present invention. Suitable treatments may include lumpectomy, mastectomy, radiation therapy, chemotherapy and hormone therapy.

The presence of a genetic variant in an individual can indicate a variation, such as an increase or decrease, in response to drugs such as chemotherapeutics. The presence of a genetic variant in an individual can also indicate a variation, such as an increase or decrease, in the toxicity of a treatment, including chemotherapy treatment. The ability to predict an individual's response to various forms of treatment may be useful in the determination and administration of therapeutic treatment. Specifically, the detection of one or more of the genetic variants of the present invention may be used to effectively prescribe drugs and determine appropriate dosages of drugs.

As is known in the art, BRCA2 is a tumor suppressor gene with an important role in cellular pathways such as DNA repair. Genetic mutations in the BRCA2 gene have been shown to be associated with cancer. Cancers, such as those linked to BRCA2-gene mutation, are treated with chemotherapeutic drugs which function by inducing DNA damage.

Genetic variants such as those disclosed in the present invention (see Table 1), are thought to cause aberrant DNA splicing leading to decreased gene expression and gene function. Accordingly, an individual having a genetic variant may have decreased BRCA2 expression and function. Thus, the presence of a genetic variant in one or more of the BRCA2 variants of the present invention may result in the loss of BRCA2 function, resulting in altered sensitivity to drugs such as DNA damaging drugs, spindle pole inhibitors and inhibitors of the DNA damage repair pathway. Methods of determining response to chemotherapeutics in an individual having a genetic variant of the present invention are described herein.

In one aspect, a patient having a deleterious mutation in a BRCA2 gene is more responsive to and is therefore treated with a DNA damaging agent such as an alkylating agent, a topoisomerase I or II, a platinum-based compound. For example alkylating agents may include, but are not limited to, cyclosporamide, nitrogen mustards, ethylenimes, alkylsulfonates, triazenes, piperazines, nitrosureas, busulfan, carboplatin, chlorambucil, cyclophosphamide, dacarbazine, ifosfamide, mechlorethamine hydrochloride, melphalan, procarbazine, thiotepa, and uracil mustard. Topoisomerase inhibitors may include, but are not limited to, topotecan (HYCAMTIN® from GlaxoSmithKline), irinotecan (CAMPTO® from Pfizer), doxorubicin, epirubicin (ELLENCE® from Pfizer), etoposide (VEPESID® from Bristol Meyers Squibb) and mitoxantrone. Platinum-based compounds may include, but are not limited to, cisplatin, oxaliplatin, tetraplatin and carboplatin. Antineoplastic compounds, may include, but are not limited to, trastuzumab, and paclitaxel.

In yet another aspect, loss of BRCA2 function is associated with resistance to spindle pole poisons including, but not limited to, abraxane, docetaxel, vinorelbine and paclitaxel (TAXOL). Spindle pole poisons lead to cell arrest and apoptosis by binding β-tubulin and stabilizing microtubules during mitosis. As such, these poisons are typically effective as chemotherapeutics in the treatment of cancer. However, the BRCA2 gene has been shown to be required for the induction of apoptosis in response to spindle poisons. See Kennedy, et al., *J. Natl. Cancer Inst.,* 96(22):1659-68 (2004). Loss of BRCA2 function may result in an increased resistance to spindle pole poisons. In other words, spindle pole poisons may be less desirable in the treatment of cancers associated with BRCA2 alteration.

In another aspect, the drug is an inhibitor of a pathway of signals and effectors that regulate the repair of DNA damage. The drug may be an inhibitor of the base excision repair (BER) pathway such as poly (ADP-ribose) polymerase (PARP). BRCA2 dysfunction has been demonstrated to dramatically increase cell sensitivity to enzymatic inhibition by PARP. This, in turn, increases chromosomal instability and cellular apoptosis. In other words, the presence of a BRCA2 genetic variant may result in increased drug response to inhibitors of the DNA damage repair pathways. See Farmer, et al., *Nature*, 434(7035):917-21 (2005). Mechanism based approaches such as PARP treatment in individuals diagnosed with BRCA2 associated cancers, is a less toxic and more specific therapy. See Wang, et al., *Genes Dev.*, 11, 2347-2358 (1997).

In another aspect, the invention provides a treatment including a compound which has a differential effect in subjects having one or more genetic variants of the present invention. This treatment is preferentially effective to treat a subject having the particular genetic variant. In another aspect, the composition is adapted to be preferentially effective based on the unit dosage, presence of additional active components, complexing of the compound with stabilizing components, or inclusion of components enhancing delivery or slowing excretion of the compound.

TABLE 3

Sequences Surrounding the BRCA2 Mutations

| SEQ ID NO | Sequence |
|---|---|
| 1 | acaaaggaaaccatcttataatcagctggcttcaactccaataatattcagagcaagggctgactctgccgctgtaccaatctcctgtaaaagaatta |
| 2 | aatctgaacataaaaacaacaattacgaaccaaacctatttaaaactccaTaaaggaaaccatcttataatcagctggcttcaactccaataatattcaa |
| 3 | tattcaaagagcaagggctgactctgccgctgtaccaatctcctgtaaaaTaattagataaattcaaattagacttaggtaagtaatgcaatatggtaga |
| 4 | agaagctccaccctataattctgaacctgcagaagaatctgaacataaaacaacaattacgaaccaaacctatttaaaactccacaaaggaaaccatct |
| 5 | tcactgaattattgtactgtttcaggaaggaatgttcccaatagtagacaaaagtcttcgcacagtgaaaactaaaatggatcaagcagatgatgttt |
| 6 | gaaaactaaaatggatcaagcagatgatgtttcctgtccacttctaaattXXXXXXXXcttgtcttagtgaaaggtatgatgaagctattatattaaaatatttaaat |
| 7 | tttagtcctgttgttctacaatgtacacatgtaacaccacaaagagataatcaggtatgattaaaaacaatgcttttttattcttagaatactagaaatg |
| 8 | attttagtcctgttgttctacaatgtacacatgtaacaccacaaagagatgtcaggtatgattaaaaacaatgcttttttattcttagaatactagaaa |
| 9 | aaaacttaacaattttccccttttttaccccccagtggtatgtgggagttgtttcatacaccaaagtttgtgaaggtaaatattctacctggtttattt |
| 10 | atcagggcatttctataaaaaataaactattttctttcctcccagggtcgcagacaccaaaacatatttctgaaagtctaggagctgaggtggatcctg |
| 11 | taaactattttctttcctcccagggtcgtcagacaccaaacatatttctgaaagtctaggagctgaggtggatcctgat |
| 12 | aactgttcagcccagtttgaagcaaatgcttttgaagcaccacttacattgcaaatgctgattcaggtacctctgtctttttttttttgtaaatagtac |
| 13 | cagtggcttcttcatttcagggtatcaaaaagtctatattcagaataagaatcacctaaagagactttcaatgcaagtttttcaggtcatatgactga |
| 14 | cttataaaggaaaaaaaataccgaaagaccaaaaatcagaactaattaacgttcagcccagtttgaagcaaatgcttttgaagcaccacttacatttgc |
| 15 | tttggaaaaacatcagggaattcatttaaagtaaatagctgcaaagaccattggaaagtcaatgccaaatgtcctagaagatgaagtatatgaaacag |
| 16 | gaaaagaaaacaaataagtttatttatgctatacatgatgaaacatcttgaaaaaaaataccgaaagaccaaaaatcagaactaattaactgt |
| 17 | agctttgaagaatgcaggtttaatatccactttgaaaaagaaaacaaataAagtttatttatgctatacatgatgaaacatcttataaaggaaaaaaaata |
| 18 | tgaagaagatagttttttcattatgttttctaaatgtagaacaaaaaatcTtacaaaaagtaagaactagcaagactaggaaaaaaattttccatgaagca |
| 19 | caccacacagaattctgtagctttgaagaatgcaggtttaatatccacttAgaaaaagaaaacaaataagtttatttatgctatacatgatgaaacatct |
| 20 | gatggagaaaataccccctattgcatatttcttcatgtgaccaaaatatttGagaaaaagacctattagacacagagaacaaaagaaagaaagattttctt |
| 21 | gaccaaaatatttcagaaaaagacctattagacacagagaacaaaagaaaaagattttcttacttcagagaattctttgccacgtatttctagcctac |
| 22 | ctttggcctgtgaatggtctcaactaaccctttcaggtctaaatggagccTagatggagaaaataccccctattgcatatttcttcatgtgaccaaaatat |
| 23 | ttttcaggtcatatgactgatccaaactttaaaaaagaaactgaagcctcaaagtggactggaaatacatactgtttgctcacagaaggaggactcct |
| 24 | acatgatgaaacatcttataaaggaaaaaaaataccgaaagaccaaaaatGagaactaattaactgttcagcccagtttgaagcaaatgcttttgaagca |
| 25 | tgtgcttctgttttatactttaacaggatttggaaaaacatcagggaattAatttaaagtaaatagctgcaaagaccacattggaaagtcaatgccaaat |
| 26 | ggtatcagatgcttcattacaaaacgcaagacaagtgttttctgaaatagtaccaagcaagtcttttccaaagtattgtttaaaagtaacgaa |
| 27 | ataatgataaaactgtaagtgaaaaaataataaatgccaactgatattaTaaaataatattgaaatgactactggcacttttgttgaagaaattactga |
| 28 | actgtgtaaactcagaaatggaaaaaacctgcagtaaagaatttaaattaTtcaaataacttaaatgttgaaggtggttcttcagaaaataatcactctat |

TABLE 3-continued

Sequences Surrounding the BRCA2 Mutations

| SEQ ID NO | Sequence |
|---|---|
| 29 | ctgtcatgcctgcaggaaggacagtgtgaaaatgatccaaaaagcaaaaaAagtttcagatataaaagaagaggtcttggctgcagcatgtcacccagtac |
| 30 | gtagacaaactgaaaatctcaaaacatcaaaaagtatctttttgaaagttTaagtacatgaaaatgtagaaaaagaaacagcaaaaagtcctgcaacttg |
| 31 | acaaatcagtccccttattcagtcattgaaaattcagccttagcttttta Gacaagttgtagtagaaaaacttctgtgagtcagacttcattacttgaag |
| 32 | aaataacttaaatgttgaaggtggttcttcagaaaataatcactctattagtttctccatatctctctcaatttcaacaagacaaacaacagttggta |
| 33 | tgtcccgaaaatgagga aatggttttgtcaaattcaagaattggaaaaaggaggagagcccct tatcttagtgggta agtgttcatttttacctttcg |
| 34 | attttccaagcaggatttta attcaaaccataatttaacacctagccaaaggcagaaattacagaacttt ctactatattagaagaatcaggaagtcag |
| 35 | aagaaagaacaaaatggacattctaagttatgaggaaacagacatagttacacaaaatactgaaagaaagtgtcccagttggtactggaaatcaacta |
| 36 | caagcctcagtcaattaatactgtatctgcacatttacagagtagtgtagXXXXXttgtttctgattgtaaaaatagtcatataaccccctcagatgttattttcc |
| 37 | tatctctcaaaaaataaacttgattctggtattgagccagtattgaagaagatcaaaaaaacactagttttttccaaagtaatatccaatgtaa |
| 38 | ttaagatagaaaatcataatgataaaactgtaagtgaaaaaaataataaaAATtgccaactgatattacaaaataatattgaaatgactactggcacttttgt |
| 39 | gttttagccatcaatgggcaaagaccctaaagtacagagaggcctgtaaaaccttgaattagcatgtgagaccattgagatcacagctgccccaaagtg |
| 40 | catctctccgaaaaacaagatacttatttaagtaacagtagcatgtctaaTAcagctattcctaccattctgatgaggtatataatgattcaggatatctct |
| 41 | cagtacaacattcaaaagtggaatacagtgatactgactttcaatcccagTaaagtcttttatatgatcatgaaaatgccagcactcttattttaactcc |
| 42 | aaaagatcaaagaacctactctgttgggttttcatacagctagcgggaaaTaagttaaaattgcaaaggaatctttggacaaagtgaaaaacctttttga |
| 43 | gaaaataatcactctattaaagtttctccatatctctctcaatttcaacagacaaacaacagttggtattaggaaccaaagtctcacttgttgagaaca |
| 44 | agaaaccagaagaattgcataacttttccttaaattctgaattacattctaagaaagaacaaaatggacattctaagttatgaggaaacagacat |
| 45 | agaatttaaattatcaaataacttaaatgttgaaggtggttcttcagaaatctattaaagtttctccatatctctctcaatttcaacaagac |
| 46 | tgtgttttatgtttaggtttattgcattcttctgtgaaaagaagctgttGacagaatgattctgaagaaccaactttgtccttaactagctcttttggg |
| 47 | ggcacaaaactgaatgtttctactgaagctctgcaaaaagctgtgaaactttagtgatattgagaatattagtgaggaaacttctgcagaggtacatc |
| 48 | aaagtgaaagacatatttacagacagtttcagtaaagtaattaaggaaaaaacgagaataaatcaaaaatttgccaaacgaaaattatggcaggttgtt |
| 49 | ctggattggagaaagtttctaaaatatcaccttgtgatgttagtttggaacttcagatatatgtaaatgtagtatagggaagcttcataagtcagtctc |
| 50 | gttttatatggagacacaggtgataaacaagcaacccaagtgtcaattaagatttggtttatgttcttgcagaggagaacaaaaatagtgtaaagc |
| 51 | tttattaccccagaagctgattctctgtcatgcctgcaggaaggacagtgAgaaaatgatccaaaaagcaaaaaagtttcagatataaaagaagaggtct |
| 52 | taaataccttggcattagataatcaaaagaaactgagcaagcctcagtcattaatactgtatctgcacatttacagagtagtgtagttgtttctgattg |
| 53 | taacacctagccaaaggcagaaattacagaactttctactatattagaaaatcaggaagtcagtttgaatttactcagtttagaaaaccaagctacat |
| 54 | ttcaaacagtactatagctgaaaatgacaaaaatcatctctccgaaaaacgatacttatttaagtaacagtagcatgtctaacagctattcctaccat |
| 55 | aatgattacatgaacaaatgggcaggactcttaggtccaatttcaaatcagttttggaggtagcttcagaacagcttcaaataaggaaatcaagctct |
| 56 | atttgtatgaaaataattcaaacagtactatagctgaaaatgacaaaaatatctctccgaaaaacaagatacttatttaagtaacagtagcatgtctaa |
| 57 | cagaacagcttcaaataaggaaatcaagctctctgaacataacattaagagagcaaaatgttcttcaaagatattgaagaacaatatcctactagtttta |
| 58 | atctggccagtttatgaaggagggaaacactcagattaaagaagatttgtGagatttaacttttttggaagttgcgaaagctcaagaagcatgtcatggt |
| 59 | aaaacaaatatagaagtttgttctacttactccaaagattcagaaaactaGtttgaaacagaagcagtagaaattgctaaagcttttatggaagatgatg |
| 60 | aacataaccaaaatatgtctggattggagaaagtttctaaaatatcacctXXXXXXXXtgtgatgttagtttggaacttcagatatatgtaaatgtagtataggga |
| 61 | agaatttaaattatcaaataacttaaatgttgaaggtggttcttcagaaaataatcactctattaaagtttctccatatctctctcaatttcaacaagac |
| 62 | catataatgtggtaaattcatctgctttctctggatttagtacagcaagtttccattttagaaagttccttacacaaagttaagggagt |

TABLE 3-continued

Sequences Surrounding the BRCA2 Mutations

| SEQ ID NO | Sequence |
|---|---|
| 63 | atttcaaaaataactgtcaatccagactctgaagaacttttctcagacaaagaataattttgtcttccaagtagctaatgaaaggaataatcttgctt |
| 64 | tatgtttaaaagtaacgaacattcagaccagctcacaagagaagaaaatAactgctatacgtactccagaacatttaatatcccaaaaaggcttttcata |
| 65 | caaaaaaatggcttagagaaggaatatttgatggtcaaccagaaagaatactgcagattatgtaggaaattatttgtatgaaaataattcaaacag |
| 66 | ctgtaaagaccttgaattagcatgtgagaccattgagatcacagctgcccaaagtgtaaagaaatgcagaattctctcaataatgataaaaaccttgtt |
| 67 | gcaaatgcatacccacaaactgtaaatgaagatatttgcgttgaggaactgtgactagctcttcaccctgcaaaaataaaaatgcagccattaaattgt |
| 68 | acccagagcactgtgtaaactcagaaatggaaaaaacctgcagtaaagaaattatcaaataacttaaatgttgaaggtggttcttcagaaaataa |
| 69 | aattaaggaaaacaacgagaataaatcaaaaatttgccaaacgaaaattaggttgttacgaggcattggatgattcagaggatattcttcataac |
| 70 | accagaagaattgcataacttttccttaaattctgaattacattctgacaaagaacaaaatggacattctaagttatgaggaaacagacatagtt |
| 71 | agaagatagtaccaagcaagtcttttccaaagtattgtttaaaagtaacgttcagaccagctcacaagagaagaaaatactgctatacgtactcca |
| 72 | aaggaatatttgatggtcaaccagaaagaataaatactgcagattatgtaTgaaattatttgtatgaaaataattcaaacagtactatagctgaaaatga |
| 73 | tgtcccgaaaatgaggaaatggttttgtcaaattcaagaattggaaaaaggagagcccttatcttagtgggtaagtgttcatttttacctttcg |
| 74 | tttcaaagtattgtttaaaagtaacgaacattcagaccagctcacaagaaaatactgctatacgtactccagaacatttaatatcccaaaagg |
| 75 | acaatatcctactagtttagcttgtgttgaaattgtaaatccttggcatGagataatcaaaagaaactgagcaagcctcagtcaattaatactgtatct |
| 76 | aattagcatgtgagaccattgagatcacagctgccccaaagtgtaaagaatgcagaattctctcaataatgataaaaaccttgtttctattgagactgt |
| 77 | tttgttctacttactccaaagattcagaaaactactttgaaacagaagcaGgtagaaattgctaaagcttttatggaagatgatgaactgacagattctaa |
| 78 | ttcctgtgaaaacaaatatagaagtttgttctacttactccaaagattcactactttgaaacagaagcagtagaaattgctaaagcttttatgga |
| 79 | acacaggtgataaacaagcaacccaagtgtcaattaaaaaagatttggttatgttcttgcagaggagaacaaaaatagtgtaaagcagcatataaaaat |
| 80 | ctgcagcatgtcacccagtacaacattcaaagtggaatacagtgatactttcaatcccagaaaagtctttatatgatcatgaaaatgccagcac |
| 81 | cgaagattgtttatgcatcatgtttctttagagccgattacctgtgtacctttcggtaagacatgtttaaattttttctaaattctaatacagtatgaga |
| 82 | acagacaaaagcaaaacattgatggacatggctctgatgatagtaaaaatgattaatgacaatgagattcatcagtttaacaaaaacaactccaatca |
| 83 | cttatatattttctccccattgcagcacaactaaggaacgtcaagagataTagaatccaaattttaccgcacctggtcaagaattttctgtctaaatctca |
| 84 | aaaaataagattaatgacaatgagattcatcagtttaacaaaaacaactcaatcaagcagcagctgtaactttcacaaagtgtgaagaagaacctttag |
| 85 | gagttgaacagtgtgttaggaatattaacttggaggaaaacagacaaaagTaaacattgatggacatggctctgatgatagtaaaaataagattaatga |
| 86 | gacatggctctgatgatagtaaaaataagattaatgacaatgagattcatTagtttaacaaaaacaactccaatcaagcagcagctgtaactttcacaaa |
| 87 | ccaaagtctttgttccaccttttaaaactaaatcacattttcacagagttTaacagtgtgttaggaatattaacttggaggaaaacagacaaaagcaaaa |
| 88 | ttcagaatgccagagatatacaggatatgcgaattaagaagaaacaaaggTaacgcgtcttccacagccaggcagtctgtatcttgcaaaaacatccac |
| 89 | ggcaacgcgtctttccacagccaggcagtctgtatcttgcaaaaacatccXXXXXXXactctgcctcgaatctctctgaaagcagcagtaggaggccaagttccctc |
| 90 | cagccaggcagtctgtatcttgcaaaaacatccactctgcctcgaatctcTtctgaaagcagcagtaggaggccaagttccctctgcgtgttctcataaac |
| 91 | attaacagcaaaaatgcagagtcttttcagtttcacactgaagattatttTtggtaaggaaagtttatggactggaaaaggaatacagttggctgatggtg |
| 92 | tggctgatggtggatggctcatacc ctccaatgatggaaaggctggaaaaTaagaattttataggtactctatgcaaaaagattgtgtgttaacttttat |
| 93 | ctgatggtggatggctcatacc ctccaatgatggaaaggctggaaaagaaTaattttataggtactctatgcaaaaagattgtgtgttaacttttatgta |
| 94 | gctgtatacgtatggcgtttctaaacattgcataaaaaattaacagcaaaaAAatgcagagtcttttcagtttcacactgaagattattttggtaaggaaagt |
| 95 | tattttgtgtagctgtatacgtatggcgtttctaaacattgcataaaaaatagcaaaaatgcagagtcttttcagtttcacactgaagattattttg |
| 96 | aggaatacagttggctgatggtggatggctcataccctccaatgatggaaAaggctggaaaagaagaattttataggtactctatgcaaaaagattgtgtg |

TABLE 3-continued

Sequences Surrounding the BRCA2 Mutations

| SEQ ID NO | Sequence |
|---|---|
| 97 | acactgaagattatttggtaaggaaagtttatggactggaaaaggaataTagttggctgatggtggatggctcatacctccaatgatggaaaggctgg |
| 98 | gtggatccaaagcttatttctagaatttgggtttataatcactatagatgAatcatatggaaactggcagctatggaatgtgcctttcctaaggaatttg |
| 99 | aagcagaagatcggctataaaaaagataatggaaagggatgacacagctgTcaaaaacacttgttctctgtgtttctgacataatttcattgagcgcaaat |
| 100 | gacagttggtcagaagattattcttcatggagcagaactggtgggctctctgatgcctgtacacctcttgaagcccccagaatctcttatgttaaaggta |
| 101 | gaagatcggctataaaaaagataatggaaagggatgacacagctgcaaaacacttgttctctgtgtttctgacataatttcattgagcgcaaatatatc |
| 102 | ataaaaaagataatggaaagggatgacacagctgcaaaacacttgttctgtgtttctgacataatttcattgagcgcaaatatatctgaaacttcta |
| 103 | gtactcggcctgctcgctggtataccaaacttggattctttcctgaccctTgaccttttcctctgcccttatcatcgcttttcagtgatggaggaaatgt |
| 104 | tatttattaatttgtccagatttctgctaacagtactcggcctgctcgctAgtataccaaacttggattctttcctgaccctagaccttttcctctgccc |
| 105 | aaccatatttaccatcacgtgcactaacaagacagcaagttcgtgctttgTaagatggtgcagagctttatgaagcagtgaagaatgcagcagacccagc |
| 106 | atctgctgaacaaaaggaacaaggtttatcaagggatgtcacaaccgtgtAgaagttgcgtattgtaagctattcaaaaaagaaaaagattcaggtaag |
| 107 | gaagagcagttaagagccttgaataatcacaggcaaatgttgaatgataacaagctcagatccagttggaaattaggaaggccatggaatctgctg |
| 108 | aaatgttgaatgataagaaacaagctcagatccagttggaaattaggaagGGgccatggaatctgctgaacaaaaggaacaaggtttatcaagggatgtcac |
| 109 | aaccgtgtggaagttgcgtattgtaagctattcaaaaaagaaaaagattGaggtaagtatgtaaatgctttgttttttatcagtttttattaacttaaaaa |
| 110 | caaacagttatactgagtatttggcgtccatcatcagatttatattctcttaacagaaggaaagagatacagaatttatcatcttgcaacttcaaaat |
| 111 | aagagatacagaatttatcatcttgcaacttcaaaatctaaaagtaaatcgaaagagctaacatacagttagcagcgacaaaaaaaactcagtatcaac |
| 112 | catcttttctccaaacagttatactgagtatttggcgtccatcatcagattAatattctctgttaacagaaggaaagagatacagaatttatcatcttgca |
| 113 | TctaaaagtaaatctgaaagagctaacatacagttagcagcgacaaaaaaXXXXXXXXXXXXXXXXXaactcagtatcaacaactaccggtacaaaccttcattgtaatttttcag |
| 114 | ctttctcatctttctccaaacagttatactgagtatttggcgtccatcatGagatttatattctctgttaacagaaggaaagagatacagaatttatcat |
| 115 | ttccattgcatctttctcatctttctccaaacagttatactgagtatttgAcgtccatcatcagatttatattctctgttaacagaaggaaagagataca |
| 116 | acttcttccattgcatctttctcatctttctccaaacagttatactgagttttggcgtccatcatcagatttatattctctgttaacagaaggaaagag |
| 117 | tggaatctccatatgttgaattttgttttgttttctgtaggtttcagatTaaattttatttcagatttaccagccacgggagcccttcacttcagcaa |
| 118 | attttagatccagactttcagccatcttgttctgaggtggacctaatagatttgtcgtttctgttgtgaaaaaaacaggtaatgcacaatatagttaa |
| 119 | tctaacacatctataataacattcttttctttttttttccattctaggactXXXXXXXtgccccttttcgtctatttgtcagacgaatgttacaatttactggcaataa |
| 120 | agcaacctccagtggcgaccagaatccaaatcaggccttcttactttattATTTgctggagattttctgtgttttctgctagtccaaaagagggccactttc |
| 121 | aagagggccactttcaagagacattcaacaaaatgaaaaatactgttgagGgtaaggttacttttcagcatcaccacacattttggtattttctatttttg |
| 122 | attcttttctttttttttccattctaggacttgccccttttcgtctatttgtGagacgaatgttacaatttactggcaataaagttttggatagaccttaat |
| 123 | ttgctgcaagcaacctccagtggcgaccagaatccaaatcaggccttcttAactttatttgctggagattttctgtgttttctgctagtccaaaagaggg |
| 124 | tgcaagcaacctccagtggcgaccagaatccaaatcaggccttcttactttTatttgctggagattttctgtgttttctgctagtccaaaagagggccac |
| 125 | ttaatgaggacattattaagcctcatatgttaattgctgcaagcaacctccagtggcgaccagaatccaaatcaggccttcttactttatttgctggaga |
| 126 | tcagacgaatgttacaatttactggcaataaagttttggatagaccttaaTtgaggacattattaagcctcatatgttaattgctgcaagcaacctccagt |
| 127 | ttaccccccagtggtatgtgggagtttgtttcatacaccaaagtttgtgaaTgtaaatattctacctggtttatttttatgacttagtaattgagaatttg |
| 128 | tatcttacagtcagaaatgaagaagcatctgaaactgtatttcctcatgagactgttgaaattgcta |
| 129 | aatagaaaatcaagaaaaatccttaaaggcttcaaaaagcactccagatgAtaaaattagcttttttatttatatctgttctccctctataggtatggtat |

TABLE 3-continued

Sequences Surrounding the BRCA2 Mutations

| SEQ ID NO | Sequence |
|---|---|
| 130 | gatattctcttagattttaactaatatgtaatataaaataattgtttcctCggcacaataaaagatcgaagattgtttatgcatcatgtttctttagagc |
| 131 | tcctgatgcctgtacacctcttgaagccccagaatctcttatgttaaaggCaaattaatttgcactcttggtaaaaatcagtcattgattcagttaaatt |
| 132 | cttgaatgttatatatgtgactttttggtgtgtgtaacacattattacaAtggatggagaagacatcatctggattatacatatttcgcaatgaaagag |
| 133 | tacctcagtcacataataaggaatgcatccctgtgtaagtgcattttggtTttctgttttgcagacttatttaccaagcattggaggaatatcgtaggta |
| 134 | tcagtcacataataaggaatgcatccctgtgtaagtgcattttggtcttcCgttttgcagacttatttaccaagcattggaggaatatcgtaggtaaaaa |
| 135 | ttctgaacctgcagaagaatctgaacataaaaacaacaattacgaaccaaGcctatttaaaactccacaaaggaaaccatcttataatcagctggcttca |
| 136 | cacttccaaagaatgcaaatttataatccagagtatatacattctcactgXXXXXXXXaattattgtactgtttcaggaaggaatgttcccaatagtagacataaaag |
| 137 | gcatcttgaatctcatacagactgcattcttgcagtaaagcaggcaatatGtggaacttctccagtggcttcttcatttcagggtatcaaaaagtctata |
| 138 | ttcatttcagggtatcaaaaagtctatattcagaataagagaatcacctaGagagactttcaatgcaagttttcaggtcatatgactgatccaaacttt |
| 139 | agagcagcatcttgaatctcatacagactgcattcttgcagtaaagcaggAaatatctggaacttctccagtggcttcttcatttcagggtatcaaaaag |
| 140 | aaaaattttccatgaagcaaacgctgatgaatgtgaaaaatctaaaaaccGagtgaaagaaaaatactcatttgtatctgaagtggaaccaaatgatact |
| 141 | ccaaaaaggcttttcatataatgtggtaaattcatctgctttctctggatGtagtacagcaagtggaaagcaagtttccattttagaaagttccttacac |
| 142 | gtgatgaaaagatcaaagaacctactctgttgggttttcatacagctagcAggaaaaaagttaaaattgcaaaggaatctttggacaaagtgaaaaacct |
| 143 | aatgtagcacgcattcacataaggttttttgctgacattcagagtgaagaaGttttacaacataaccaaaatatgtctggattggagaaagtttctaaaat |
| 144 | cgaaaattatggcaggttgttacgaggcattggatgattcagaggatattGttcataactctctagataatgatgaatgtagcacgcattcacataaggt |
| 145 | cttaaatgttgaaggtggttcttcagaaaataatcactctattaaagtttAtccatatctctctcaatttcaacaagacaaacaacagttggtattagga |
| 146 | agacttgacttgtgtaaacgaacccatttttcaagaactctaccatggtttCatatggagacacaggtgataaacaagcaacccaagtgtcaattaaaaaa |
| 147 | tttaaaatcggacatctccttgaatatagataaaataccagaaaaaaataTtgattacatgaacaaatgggcaggactcttaggtccaatttcaaatcac |
| 148 | tcttcactattcacctacgtctagacaaaatgtatcaaaaatacttcctcAtgttgataagagaaacccagagcactgtgtaaactcagaaatggaaaaa |
| 149 | gatttagtacagcaagtggaaagcaagtttccattttagaaagttccttaAacaaagttaagggagtgttagaggaatttgatttaatcagaactgagca |
| 150 | gattaaagaagatttgtcagatttaactttttttggaagttgcgaaagctcGagaagcatgtcatggtaatacttcaaataaagaacagttaactgctact |
| 151 | aaatggaaaaaacctgcagtaaagaatttaaattatcaaataacttaaatTttgaaggtggttcttcagaaaataatcactctattaaagttctccata |
| 152 | agttgtagtagaaaaacttctgtgagtcagacttcattacttgaagcaaaCaaatggcttagagaaggaatatttgatggtcaaccagaaagaataaata |
| 153 | aaccaagctacatattgcagaagagtacatttgaagtgcctgaaaaccagGtgactatcttaaagaccacttctgaggaatgcagagatgctgatcttca |
| 154 | tattcataaagatgaaacggacttgctatttactgatcagcacaacatatAtcttaaattatctggccagtttatgaaggagggaaacactcagattaaa |
| 155 | tctcagacaatgagaataattttgtcttccaagtagctaatgaaaggaatGatcttgctttaggaaatactaaggaacttcatgaaacagacttgacttg |
| 156 | taacttagaatttgatggcagtgattcaagtaaaaatgatactgtttgtaCtcataaagatgaaacggacttgctatttactgatcagcacaacatatgt |
| 157 | taatattgaaatgactactggcacttttgttgaagaaattactgaaaattGcaagagaaatactgaaaatgaagataacaaatatactgctgccagtaga |
| 158 | gataatagaaatcaagaaaaatccttaaaggcttcaaaaagcactccagTtggtaaaattagcttttatttatatctgttctccctctataggtatgg |
| 159 | ctttggaaaaatcttcaagcaatttagcagtttcaggacatcccattttatAaagtttctgctacaagaaatgaaaaatgagacacttgattactacagg |
| 160 | ctggccaggggttgtgcttttaaatttcaattttattttttgctaagtatGtattctttgatagatttaattacaagtcttcagaatgccagagatatac |
| 161 | tttattgtgtgatacatgtttactttaaattgttttctttttgtgtgtattttgtgtagctgtatacgtatggcgtttctaaacattgcataaa |
| 162 | tctagttacaatagatggaactttttttgttctgattgcttttttattccaaCatcttaaatggtcacagggttatttcagtgaagagcagttaagagcctt |
| 163 | cagttttgataagtgcttgttagtttatggaatctccatatgttgaatttCtgttttgttttctgtaggtttcagatgaaatttttatttcagatttacca |
| 164 | atgaaatttatttcagatttaccagccacgggagccccttcacttcagcGaattttagatccagacttcagccatcttgttctgaggtggacctaat |
| 165 | cactttcaagagacattcaacaaaatgaaaaatactgttgaggtaaggttCcttttcagcatcaccacacatttggtattttctattttgacagtcca |

TABLE 3-continued

Sequences Surrounding the BRCA2 Mutations

| SEQ ID NO | Sequence |
|---|---|
| 166 | aaacaagcttatgcatatactgcatgcaaatgatcccaagtggtccacccAaactaaagactgtacttcagggccgtacactgctcaaatcattcctggt |
| 167 | aaagaaaaagaactgaattctcctcagatgactccatttaaaaaattcaGtgaaatttctcttttggaaagtaattcaatagctgacgaagaacttgca |
| 168 | cattgataaatacccaagctcttttgtctggttcaacaggagaaaaacaaCttatatctgtcagtgaatccactaggactgctcccaccagttcagaaga |
| 169 | aaagtaattcaatagctgacgaagaacttgcattgataaatacccaagctGttttgtctggttcaacaggagaaaaacaatttatatctgtcagtgaatc |
| 170 | tctcagactgaaacgacgttgtactacatctctgatcaaagaacaggagaAttcccaggccagtacggaagaatgtgagaaaaataagcaggacacaatt |
| 171 | cagtacggaagaatgtgagaaaaataagcaggacacaattacaactaaaaCatatatctaagcatttgcaaaggcgacaataaattattgacgcttaacc |
| 172 | gaagaatgtgagaaaaataagcaggacacaattacaactaaaaaatatatGtaagcatttgcaaaggcgacaataaattattgacgcttaacctttccag |
| 173 | ttcaaatgtagcacatcagaagccctttgagagtggaagtgacaaaatctTcaaggaagttgtaccgtctttggcctgtgaatggtctcaactaacccctt |
| 174 | ttatgtttttctaaatgtagaacaaaaaatctacaaaaagtaagaactagAaagactaggaaaaaaattttccatgaagcaaacgctgatgaatgtgaaa |
| 175 | atctggaacttctccagtggcttcttcatttcagggtatcaaaaagtctaCattcagaataagagaatcacctaaagagactttcaatgcaagtttttca |
| 176 | taatatccactttgaaaaagaaaacaaataagtttatttatgctatacatCatgaaacatcttataaaggaaaaaaaataccgaaagaccaaaaatcaga |
| 177 | tttgccacgtatttctagcctaccaaaatcagagaagccattaaatgaggGaacagtggtaaataagagagatgaagagcagcatcttgaatctcataca |
| 178 | acgaacccattttcaagaactctaccatggttttatatggagacacaggtAataaacaagcaacccaagtgtcaattaaaaaagatttggtttatgttct |
| 179 | acaaaatgtatcaaaaatacttcctcgtgttgataagagaaacccagagcGctgtgtaaactcagaaatggaaaaaacctgcagtaaagaatttaaatta |
| 180 | agcatgtcatggtaatacttcaaataaagaacagttaactgctactaaaaTggagcaaaatataaaagattttgagacttctgatacattttttcagact |
| 181 | taagatagaaaatcataatgataaaactgtaagtgaaaaaaataataaatAccaactgatattacaaaataatattgaaatgactactggcactttgtt |
| 182 | agatttaaaatcggacatctccttgaatatagataaaataccagaaaaaaGtaatgattacatgaacaaatgggcaggactcttaggtccaatttcaaat |
| 183 | tgaggtatataatgattcaggatatctctcaaaaaataaacttgattctgAtattgagccagtattgaagaatgttgaagatcaaaaaaacactagtttt |
| 184 | gccaaacgaaaattatggcaggttgttacgaggcattggatgattcagagAatattcttcataactctctagataatgatgaatgtagcacgcattcaca |
| 185 | tgaacagtgtgttaggaatattaacttggaggaaaacagacaaaagcaaaTcattgatggacatggctctgatgatagtaaaaataagattaatgacaat |
| 186 | acaaaggcaacgcgtctttccacagccaggcagtctgtatcttgcaaaaaTatccactctgcctcgaatctctctgaaagcagcagtaggaggccaagtt |
| 187 | tatctgaaacttctagcaataaaactagtagtgcagatacccaaaaagtgTccattattgaacttacagatgggtggtatgctgttaaggcccagttaga |
| 188 | tcctaaaatatgcatttttgttttcacttttagatatgatacggaaattgGtagaagcagaagatcggctataaaaaagataatggaaagggatgacaca |
| 189 | catatttcgcaatgaaagagaggaagaaaaggaagcagcaaaatatgtggCggcccaacaaaagagactagaagccttattcactaaaattcaggaggaa |
| 190 | gtgactttttggtgtgtgtaacacattattacagtggatggagaagacaCcatctggattatacatatttcgcaatgaaagagaggaagaaaaggaagc |
| 191 | caaatgttaatgataagaaacaagctcagatccagttggaaattaggaaTgccatggaatctgctgaacaaaaggaacaaggtttatcaagggatgtca |
| 192 | atattctctgttaacagaaggaaagagatacagaatttatcatcttgcaaTttcaaaatctaaaagtaaatctgaaagagctaacatacagttagcagcg |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting a mutation in a BRCA2 allele comprising:
   analyzing a BRCA2 nucleic acid from a sample obtained from a human subject; and
   detecting a mutation in said nucleic acid wherein said mutation results in the deletion of five nucleotides beginning at position 4,633 of a BRCA2 cDNA.

2. The method of claim 1 comprising sequencing said nucleic acid.

3. A method of genotyping, comprising:
   obtaining a tissue sample or cells from a human patient identified as, or suspected of, having an increased predisposition to breast and ovarian cancer; and
   detecting in said tissue sample or cells a deletion of five nucleotides in a BRCA2 allele beginning at the cDNA position of 4,633.

4. The method of claim 3 comprising amplifying a nucleic acid comprising SEQ ID NO:44.

5. A method for detecting a mutation in a BRCA2 allele comprising:
   analyzing a nucleic acid from a tissue sample or cells obtained from a human subject; and
   detecting in said nucleic acid a mutation resulting in a BRCA2 allele comprising SEQ ID NO:44.

6. The method of claim 5 wherein said tissue sample or cells were obtained from a patient identified as, or suspected of, having an increased predisposition to breast and ovarian cancer.

7. The method of claim 5 comprising hybridizing a probe to said BRCA2 allele.

* * * * *

SEQUENCE LISTING

<160> NUMBER OF SEQ ID NOS: 192

<210> SEQ ID NO 1

-continued

```
<211> LENGTH: 98
<212> TYPE: DNA
<213> ORGANISM: Homo sapiens

<400> SEQUENCE: 1
acaaaggaaa ccatcttata atcagctggc ttcaactcca ataatattca gagcaagggc    60
tgactctgcc gctgtaccaa tctcctgtaa aagaatta                            98

<210> SEQ ID NO 2
<211> LENGTH: 100
<212> TYPE: DNA
<213> ORGANISM: Homo sapiens

<400> SEQUENCE: 2
aatctgaaca taaaaacaac aattacgaac caaacctatt taaaactcca taaaggaaac    60
catcttataa tcagctggct tcaactccaa taatattcaa                         100

<210> SEQ ID NO 3
<211> LENGTH: 100
<212> TYPE: DNA
<213> ORGANISM: Homo sapiens

<400> SEQUENCE: 3
tattcaaaga gcaagggctg actctgccgc tgtaccaatc tcctgtaaaa taattagata    60
aattcaaatt agacttaggt aagtaatgca atatggtaga                         100

<210> SEQ ID NO 4
<211> LENGTH: 99
<212> TYPE: DNA
<213> ORGANISM: Homo sapiens

<400> SEQUENCE: 4
agaagctcca ccctataatt ctgaacctgc agaagaatct gaacataaaa caacaattac    60
gaaccaaacc tatttaaaac tccacaaagg aaaccatct                           99

<210> SEQ ID NO 5
<211> LENGTH: 98
<212> TYPE: DNA
<213> ORGANISM: Homo sapiens

<400> SEQUENCE: 5
tcactgaatt attgtactgt ttcaggaagg aatgttccca atagtagaca aaagtcttcg    60
cacagtgaaa actaaaatgg atcaagcaga tgatgttt                            98

<210> SEQ ID NO 6
<211> LENGTH: 108
<212> TYPE: DNA
<213> ORGANISM: Homo sapiens
<220> FEATURE:
<221> NAME/KEY: misc_feature
<222> LOCATION: (51)..(58)
<223> OTHER INFORMATION: n is a, c, g, or t

<400> SEQUENCE: 6
gaaaactaaa atggatcaag cagatgatgt ttcctgtcca cttctaaatt nnnnnnnnct    60
tgtcttagtg aaaggtatga tgaagctatt atattaaaat atttaaat                108

<210> SEQ ID NO 7
<211> LENGTH: 99
<212> TYPE: DNA
<213> ORGANISM: Homo sapiens
```

<400> SEQUENCE: 7
tttagtcctg ttgttctaca atgtacacat gtaacaccac aaagagataa tcaggtatga    60
ttaaaaacaa tgcttttat tcttagaata ctagaaatg                            99

<210> SEQ ID NO 8
<211> LENGTH: 98
<212> TYPE: DNA
<213> ORGANISM: Homo sapiens

<400> SEQUENCE: 8
attttagtcc tgttgttcta caatgtacac atgtaacacc acaaagagat gtcaggtatg    60
attaaaaaca atgctttta ttcttagaat actagaaa                             98

<210> SEQ ID NO 9
<211> LENGTH: 99
<212> TYPE: DNA
<213> ORGANISM: Homo sapiens

<400> SEQUENCE: 9
aaaacttaac aatttccc ttttttacc cccagtggta tgtgggagtt gtttcataca       60
ccaaagtttg tgaaggtaaa tattctacct ggtttatt                            99

<210> SEQ ID NO 10
<211> LENGTH: 99
<212> TYPE: DNA
<213> ORGANISM: Homo sapiens

<400> SEQUENCE: 10
atcagggcat ttctataaaa aataaactat tttctttcct cccagggtcg cagacaccaa    60
aacatatttc tgaaagtcta ggagctgagg tggatcctg                           99

<210> SEQ ID NO 11
<211> LENGTH: 79
<212> TYPE: DNA
<213> ORGANISM: Homo sapiens

<400> SEQUENCE: 11 taaactatt tctttcctcc cagggtcgtc agacaccaaa catatttctg aaagtctagg     60
agctgaggtg gatcctgat                                                 79

<210> SEQ ID NO 12
<211> LENGTH: 99
<212> TYPE: DNA
<213> ORGANISM: Homo sapiens

<400> SEQUENCE: 12
aactgttcag cccagtttga agcaaatgct tttgaagcac cacttacatt gcaaatgctg    60
attcaggtac ctctgtcttt ttttttttgt aaatagtac                           99

<210> SEQ ID NO 13
<211> LENGTH: 98
<212> TYPE: DNA
<213> ORGANISM: Homo sapiens

<400> SEQUENCE: 13
cagtggcttc ttcatttcag ggtatcaaaa agtctatatt cagaataaga atcacctaaa    60
gagactttca atgcaagttt ttcaggtcat atgactga                            98

<210> SEQ ID NO 14

```
<211> LENGTH: 99
<212> TYPE: DNA
<213> ORGANISM: Homo sapiens

<400> SEQUENCE: 14
cttataaagg aaaaaaaata ccgaaagacc aaaaatcaga actaattaac gttcagccca      60
gtttgaagca aatgcttttg aagcaccact tacatttgc                            99

<210> SEQ ID NO 15
<211> LENGTH: 98
<212> TYPE: DNA
<213> ORGANISM: Homo sapiens

<400> SEQUENCE: 15
tttggaaaaa catcagggaa ttcatttaaa gtaaatagct gcaaagacca ttggaaagtc      60
aatgccaaat gtcctagaag atgaagtata tgaaacag                             98

<210> SEQ ID NO 16
<211> LENGTH: 94
<212> TYPE: DNA
<213> ORGANISM: Homo sapiens

<400> SEQUENCE: 16 gaaaagaaa acaaataagt ttatttatgc tatacatgat gaaacatctt gaaaaaaaat       60
accgaaagac caaaaatcag aactaattaa ctgt                                 94

<210> SEQ ID NO 17
<211> LENGTH: 101
<212> TYPE: DNA
<213> ORGANISM: Homo sapiens

<400> SEQUENCE: 17
agctttgaag aatgcaggtt taatatccac tttgaaaaag aaaacaaata agtttatttt      60
atgctataca tgatgaaaca tcttataaag gaaaaaaaat a                         101

<210> SEQ ID NO 18
<211> LENGTH: 101
<212> TYPE: DNA
<213> ORGANISM: Homo sapiens

<400> SEQUENCE: 18
tgaagaagat agttttttcat tatgttttttc taaatgtaga acaaaaaatc ttacaaaaag    60
taagaactag caagactagg aaaaaaattt tccatgaagc a                         101

<210> SEQ ID NO 19
<211> LENGTH: 100
<212> TYPE: DNA
<213> ORGANISM: Homo sapiens

<400> SEQUENCE: 19
caccacacag aattctgtag cttttgaagaa tgcaggttta atatccactt agaaaaagaa    60
aacaaataag tttatttatg ctatacatga tgaaacatct                           100

<210> SEQ ID NO 20
<211> LENGTH: 100
<212> TYPE: DNA
<213> ORGANISM: Homo sapiens

<400> SEQUENCE: 20
gatggagaaa ataccccctat tgcatatttc ttcatgtgac caaaatatttt gagaaaaga    60
```

```
cctattagac acagagaaca aaagaaagaa agattttctt                            100
```

<210> SEQ ID NO 21
<211> LENGTH: 98
<212> TYPE: DNA
<213> ORGANISM: Homo sapiens

<400> SEQUENCE: 21

```
gaccaaaata tttcagaaaa agacctatta gacacagaga acaaagaaa aagattttct       60 tacttcagag aattctttgc cacgtatttc tagcctac                              98
```

<210> SEQ ID NO 22
<211> LENGTH: 100
<212> TYPE: DNA
<213> ORGANISM: Homo sapiens

<400> SEQUENCE: 22

```
ctttggcctg tgaatggtct caactaaccc tttcaggtct aaatggagcc tagatggaga      60
aaatacccct attgcatatt tcttcatgtg accaaaatat                            100
```

<210> SEQ ID NO 23
<211> LENGTH: 98
<212> TYPE: DNA
<213> ORGANISM: Homo sapiens

<400> SEQUENCE: 23

```
ttttcaggtc atatgactga tccaaacttt aaaaagaaa ctgaagcctc aaagtggact       60
ggaaatacat actgtttgct cacagaagga ggactcct                              98
```

<210> SEQ ID NO 24
<211> LENGTH: 100
<212> TYPE: DNA
<213> ORGANISM: Homo sapiens

<400> SEQUENCE: 24

```
acatgatgaa acatcttata aaggaaaaaa aataccgaaa gaccaaaaat gagaactaat      60
taactgttca gcccagtttg aagcaaatgc ttttgaagca                            100
```

<210> SEQ ID NO 25
<211> LENGTH: 100
<212> TYPE: DNA
<213> ORGANISM: Homo sapiens

<400> SEQUENCE: 25

```
tgtgcttctg ttttatactt taacaggatt tggaaaaaca tcagggaatt aatttaaagt      60
aaatagctgc aaagaccaca ttggaaagtc aatgccaaat                            100
```

<210> SEQ ID NO 26
<211> LENGTH: 93
<212> TYPE: DNA
<213> ORGANISM: Homo sapiens

<400> SEQUENCE: 26

```
ggtatcagat gcttcattac aaaacgcaag acaagtgttt tctgaaatag taccaagcaa      60
gtcttttcca agtattgtt taaaagtaac gaa                                    93
```

<210> SEQ ID NO 27
<211> LENGTH: 100
<212> TYPE: DNA
<213> ORGANISM: Homo sapiens -continued

```
<400> SEQUENCE: 27
ataatgataa aactgtaagt gaaaaaaata ataaatgcca actgatatta taaaataata     60
ttgaaatgac tactggcact tttgttgaag aaattactga                          100

<210> SEQ ID NO 28
<211> LENGTH: 101
<212> TYPE: DNA
<213> ORGANISM: Homo sapiens

<400> SEQUENCE: 28
actgtgtaaa ctcagaaatg gaaaaaacct gcagtaaaga atttaaatta ttcaaataac     60
ttaaatgttg aaggtggttc ttcagaaaat aatcactcta t                       101

<210> SEQ ID NO 29
<211> LENGTH: 101
<212> TYPE: DNA
<213> ORGANISM: Homo sapiens

<400> SEQUENCE: 29
ctgtcatgcc tgcaggaagg acagtgtgaa aatgatccaa aaagcaaaaa aagtttcaga     60 tataaagaa gaggtcttgg ctgcagcatg tcacccagta c                        101

<210> SEQ ID NO 30
<211> LENGTH: 100
<212> TYPE: DNA
<213> ORGANISM: Homo sapiens

<400> SEQUENCE: 30
gtagacaaac tgaaaatctc aaaacatcaa aaagtatctt tttgaaagtt taagtacatg     60
aaaatgtaga aaagaaaca gcaaaaagtc ctgcaacttg                          100

<210> SEQ ID NO 31
<211> LENGTH: 100
<212> TYPE: DNA
<213> ORGANISM: Homo sapiens

<400> SEQUENCE: 31
acaaatcagt cccttattc agtcattgaa aattcagcct tagctttta gacaagttgt      60 agtagaaaaa cttctgtgag tcagacttca ttacttgaag                         100

<210> SEQ ID NO 32
<211> LENGTH: 98
<212> TYPE: DNA
<213> ORGANISM: Homo sapiens

<400> SEQUENCE: 32
aaataactta aatgttgaag gtggttcttc agaaaataat cactctatta gtttctccat     60
atctctctca atttcaacaa gacaaacaac agttggta                            98

<210> SEQ ID NO 33
<211> LENGTH: 98
<212> TYPE: DNA
<213> ORGANISM: Homo sapiens

<400> SEQUENCE: 33
tgtcccgaaa atgaggaaat ggttttgtca aattcaagaa ttggaaaaag gaggagagcc     60
ccttatctta gtgggtaagt gttcattttt acctttcg                            98

<210> SEQ ID NO 34
```

<211> LENGTH: 99
<212> TYPE: DNA
<213> ORGANISM: Homo sapiens

<400> SEQUENCE: 34
attttccaag caggatttta attcaaacca taatttaaca cctagccaaa ggcagaaatt    60
acagaacttt ctactatatt agaagaatca ggaagtcag                          99

<210> SEQ ID NO 35
<211> LENGTH: 98
<212> TYPE: DNA
<213> ORGANISM: Homo sapiens

<400> SEQUENCE: 35
aagaaagaac aaaatggaca ttctaagtta tgaggaaaca gacatagtta cacaaaatac    60
tgaaagaaag tgtcccagtt ggtactggaa atcaacta                           98

<210> SEQ ID NO 36
<211> LENGTH: 105
<212> TYPE: DNA
<213> ORGANISM: Homo sapiens
<220> FEATURE:
<221> NAME/KEY: misc_feature
<222> LOCATION: (51)..(55)
<223> OTHER INFORMATION: n is a, c, g, or t

<400> SEQUENCE: 36
caagcctcag tcaattaata ctgtatctgc acatttacag agtagtgtag nnnnnttgtt    60
tctgattgta aaatagtca tataacccct cagatgttat tttcc                   105

<210> SEQ ID NO 37
<211> LENGTH: 93
<212> TYPE: DNA
<213> ORGANISM: Homo sapiens

<400> SEQUENCE: 37
tatctctcaa aaataaact tgattctggt attgagccag tattgaagaa gatcaaaaaa    60
acactagttt ttccaaagta atatccaatg taa                                93

<210> SEQ ID NO 38
<211> LENGTH: 103
<212> TYPE: DNA
<213> ORGANISM: Homo sapiens

<400> SEQUENCE: 38
ttaagataga aaatcataat gataaaactg taagtgaaaa aaataataaa aattgccaac    60
tgatattaca aaataatatt gaaatgacta ctggcacttt tgt                    103

<210> SEQ ID NO 39
<211> LENGTH: 99
<212> TYPE: DNA
<213> ORGANISM: Homo sapiens

<400> SEQUENCE: 39
gttttagcca tcaatgggca aagaccctaa agtacagaga ggcctgtaaa accttgaatt    60
agcatgtgag accattgaga tcacagctgc cccaaagtg                          99

<210> SEQ ID NO 40
<211> LENGTH: 102
<212> TYPE: DNA
<213> ORGANISM: Homo sapiens

```
<400> SEQUENCE: 40
catctctccg aaaaacaaga tacttattta agtaacagta gcatgtctaa tacagctatt    60
cctaccattc tgatgaggta tataatgatt caggatatct ct                      102

<210> SEQ ID NO 41
<211> LENGTH: 100
<212> TYPE: DNA
<213> ORGANISM: Homo sapiens

<400> SEQUENCE: 41
cagtacaaca ttcaaaagtg gaatacagtg atactgactt tcaatcccag taaagtcttt    60
tatatgatca tgaaaatgcc agcactctta ttttaactcc                        100

<210> SEQ ID NO 42
<211> LENGTH: 100
<212> TYPE: DNA
<213> ORGANISM: Homo sapiens

<400> SEQUENCE: 42
aaaagatcaa agaacctact ctgttgggtt tcatacagc tagcgggaaa taagttaaaa    60
ttgcaaagga atctttggac aaagtgaaaa acctttttga                        100

<210> SEQ ID NO 43
<211> LENGTH: 99
<212> TYPE: DNA
<213> ORGANISM: Homo sapiens

<400> SEQUENCE: 43 gaaataatc actctattaa agtttctcca tatctctctc aatttcaaca gacaaacaac    60
agttggtatt aggaaccaaa gtctcacttg ttgagaaca                          99

<210> SEQ ID NO 44
<211> LENGTH: 95
<212> TYPE: DNA
<213> ORGANISM: Homo sapiens

<400> SEQUENCE: 44
agaaaccaga agaattgcat aactttttcct taaattctga attacattct aagaaagaac   60
aaaatggaca ttctaagtta tgaggaaaca gacat                              95

<210> SEQ ID NO 45
<211> LENGTH: 92
<212> TYPE: DNA
<213> ORGANISM: Homo sapiens

<400> SEQUENCE: 45
agaatttaaa ttatcaaata acttaaatgt tgaaggtggt tcttcagaaa tctattaaag    60
tttctccata tctctctcaa tttcaacaag ac                                 92

<210> SEQ ID NO 46
<211> LENGTH: 100
<212> TYPE: DNA
<213> ORGANISM: Homo sapiens

<400> SEQUENCE: 46
tgtgttttta tgtttaggtt tattgcattc ttctgtgaaa agaagctgtt gacagaatga    60
ttctgaagaa ccaactttgt ccttaactag ctcttttggg                        100

<210> SEQ ID NO 47
```

```
<211> LENGTH: 98
<212> TYPE: DNA
<213> ORGANISM: Homo sapiens

<400> SEQUENCE: 47
ggcacaaaac tgaatgtttc tactgaagct ctgcaaaaag ctgtgaaact ttagtgatat    60
tgagaatatt agtgaggaaa cttctgcaga ggtacatc                            98

<210> SEQ ID NO 48
<211> LENGTH: 99
<212> TYPE: DNA
<213> ORGANISM: Homo sapiens

<400> SEQUENCE: 48
aaagtgaaag acatatttac agacagtttc agtaaagtaa ttaaggaaaa acgagaata    60 aatcaaaaat ttgccaaacg aaaattatgg caggttgtt                          99

<210> SEQ ID NO 49
<211> LENGTH: 99
<212> TYPE: DNA
<213> ORGANISM: Homo sapiens

<400> SEQUENCE: 49
ctggattgga gaaagtttct aaaatatcac cttgtgatgt tagtttggaa cttcagatat    60
atgtaaatgt agtataggga agcttcataa gtcagtctc                          99

<210> SEQ ID NO 50
<211> LENGTH: 96
<212> TYPE: DNA
<213> ORGANISM: Homo sapiens

<400> SEQUENCE: 50
gttttatatg gagacacagg tgataaacaa gcaacccaag tgtcaattaa gatttggttt    60
atgttcttgc agaggagaac aaaaatagtg taaagc                             96

<210> SEQ ID NO 51
<211> LENGTH: 100
<212> TYPE: DNA
<213> ORGANISM: Homo sapiens

<400> SEQUENCE: 51
tttattaccc cagaagctga ttctctgtca tgcctgcagg aaggacagtg agaaaatgat    60
ccaaaaagca aaaagtttc agatataaaa gaagaggtct                         100

<210> SEQ ID NO 52
<211> LENGTH: 99
<212> TYPE: DNA
<213> ORGANISM: Homo sapiens

<400> SEQUENCE: 52
taaatacctt ggcattagat aatcaaaaga aactgagcaa gcctcagtca ttaatactgt    60
atctgcacat ttacagagta gtgtagttgt ttctgattg                          99

<210> SEQ ID NO 53
<211> LENGTH: 99
<212> TYPE: DNA
<213> ORGANISM: Homo sapiens

<400> SEQUENCE: 53
taacacctag ccaaaaggca gaaattacag aactttctac tatattagaa aatcaggaag    60
```

```
tcagtttgaa tttactcagt ttagaaaacc aagctacat                                99
```

<210> SEQ ID NO 54
<211> LENGTH: 98
<212> TYPE: DNA
<213> ORGANISM: Homo sapiens

<400> SEQUENCE: 54

```
ttcaaacagt actatagctg aaaatgacaa aaatcatctc tccgaaaaac gatacttatt        60
taagtaacag tagcatgtct aacagctatt cctaccat                                98
```

<210> SEQ ID NO 55
<211> LENGTH: 98
<212> TYPE: DNA
<213> ORGANISM: Homo sapiens

<400> SEQUENCE: 55

```
aatgattaca tgaacaaatg ggcaggactc ttaggtccaa tttcaaatca gttttggagg        60
tagcttcaga acagcttcaa ataaggaaat caagctct                                98
```

<210> SEQ ID NO 56
<211> LENGTH: 99
<212> TYPE: DNA
<213> ORGANISM: Homo sapiens

<400> SEQUENCE: 56

```
atttgtatga aaataattca aacagtacta tagctgaaaa tgacaaaaat atctctccga        60
aaaacaagat acttatttaa gtaacagtag catgtctaa                               99
```

<210> SEQ ID NO 57
<211> LENGTH: 99
<212> TYPE: DNA
<213> ORGANISM: Homo sapiens

<400> SEQUENCE: 57

```
cagaacagct tcaaataagg aaatcaagct ctctgaacat aacattaaga gagcaaaatg        60
ttcttcaaag atattgaaga acaatatcct actagttta                               99
```

<210> SEQ ID NO 58
<211> LENGTH: 100
<212> TYPE: DNA
<213> ORGANISM: Homo sapiens

<400> SEQUENCE: 58

```
atctggccag tttatgaagg agggaaacac tcagattaaa gaagatttgt gagatttaac        60
ttttttggaa gttgcgaaag ctcaagaagc atgtcatggt                             100
```

<210> SEQ ID NO 59
<211> LENGTH: 100
<212> TYPE: DNA
<213> ORGANISM: Homo sapiens

<400> SEQUENCE: 59

```
aaaacaaata tagaagtttg ttctacttac tccaaagatt cagaaaacta gtttgaaaca        60
gaagcagtag aaattgctaa agcttttatg gaagatgatg                             100
```

<210> SEQ ID NO 60
<211> LENGTH: 108
<212> TYPE: DNA
<213> ORGANISM: Homo sapiens
<220> FEATURE:

```
<221> NAME/KEY: misc_feature
<222> LOCATION: (51)..(58)
<223> OTHER INFORMATION: n is a, c, g, or t

<400> SEQUENCE: 60
aacataacca aaatatgtct ggattggaga aagtttctaa aatatcacct nnnnnnnntg       60
tgatgttagt ttggaaactt cagatatatg taaatgtagt atagggaa                  108

<210> SEQ ID NO 61
<211> LENGTH: 99
<212> TYPE: DNA
<213> ORGANISM: Homo sapiens

<400> SEQUENCE: 61
agaatttaaa ttatcaaata acttaaatgt tgaaggtggt tcttcagaaa taatcactct       60
attaaagttt ctccatatct ctctcaattt caacaagac                             99

<210> SEQ ID NO 62
<211> LENGTH: 89
<212> TYPE: DNA
<213> ORGANISM: Homo sapiens

<400> SEQUENCE: 62
catataatgt ggtaaattca tctgctttct ctggatttag tacagcaagt ttccatttta       60
gaaagttcct tacacaaagt taagggagt                                        89

<210> SEQ ID NO 63
<211> LENGTH: 98
<212> TYPE: DNA
<213> ORGANISM: Homo sapiens

<400> SEQUENCE: 63
atttcaaaaa taactgtcaa tccagactct gaagaacttt tctcagacaa agaataattt       60
tgtcttccaa gtagctaatg aaaggaataa tcttgctt                              98

<210> SEQ ID NO 64
<211> LENGTH: 101
<212> TYPE: DNA
<213> ORGANISM: Homo sapiens

<400> SEQUENCE: 64
tattgtttaa aagtaacgaa cattcagacc agctcacaag agaagaaaat aactgctata       60
cgtactccag aacatttaat atcccaaaaa ggcttttcat a                         101

<210> SEQ ID NO 65
<211> LENGTH: 96
<212> TYPE: DNA
<213> ORGANISM: Homo sapiens

<400> SEQUENCE: 65
caaaaaaatg gcttagagaa ggaatatttg atggtcaacc agaaagaata ctgcagatta       60
tgtaggaaat tatttgtatg aaaataattc aaacag                                96

<210> SEQ ID NO 66
<211> LENGTH: 99
<212> TYPE: DNA
<213> ORGANISM: Homo sapiens

<400> SEQUENCE: 66
ctgtaaagac cttgaattag catgtgagac cattgagatc acagctgccc aaagtgtaaa       60
```

```
gaaatgcaga attctctcaa taatgataaa aaccttgtt                        99

<210> SEQ ID NO 67
<211> LENGTH: 99
<212> TYPE: DNA
<213> ORGANISM: Homo sapiens

<400> SEQUENCE: 67
gcaaatgcat acccacaaac tgtaaatgaa gatatttgcg ttgaggaact gtgactagct    60
cttcaccctg caaaaataaa aatgcagcca ttaaattgt                          99

<210> SEQ ID NO 68
<211> LENGTH: 95
<212> TYPE: DNA
<213> ORGANISM: Homo sapiens

<400> SEQUENCE: 68
acccagagca ctgtgtaaac tcagaaatgg aaaaaacctg cagtaaagaa attatcaaat    60
aacttaaatg ttgaaggtgg ttcttcagaa aataa                              95

<210> SEQ ID NO 69
<211> LENGTH: 95
<212> TYPE: DNA
<213> ORGANISM: Homo sapiens

<400> SEQUENCE: 69
aattaaggaa acaacgaga ataaatcaaa aatttgccaa acgaaaatta ggttgttacg     60
aggcattgga tgattcagag gatattcttc ataac                              95

<210> SEQ ID NO 70
<211> LENGTH: 95
<212> TYPE: DNA
<213> ORGANISM: Homo sapiens

<400> SEQUENCE: 70
accagaagaa ttgcataact tttccttaaa ttctgaatta cattctgaca aagaacaaaa    60
tggacattct aagttatgag gaaacagaca tagtt                              95

<210> SEQ ID NO 71
<211> LENGTH: 96
<212> TYPE: DNA
<213> ORGANISM: Homo sapiens

<400> SEQUENCE: 71
agaagatagt accaagcaag tcttttccaa agtattgttt aaaagtaacg ttcagaccag    60
ctcacaagag aagaaaatac tgctatacgt actcca                             96

<210> SEQ ID NO 72
<211> LENGTH: 100
<212> TYPE: DNA
<213> ORGANISM: Homo sapiens

<400> SEQUENCE: 72
aaggaatatt tgatggtcaa ccagaaagaa taaatactgc agattatgta tgaaattatt    60
tgtatgaaaa taattcaaac agtactatag ctgaaaatga                         100

<210> SEQ ID NO 73
<211> LENGTH: 95
<212> TYPE: DNA
<213> ORGANISM: Homo sapiens
```

-continued

<400> SEQUENCE: 73
tgtcccgaaa atgaggaaat ggttttgtca aattcaagaa ttggaaaaag gagagcccct    60
tatcttagtg ggtaagtgtt catttttacc tttcg                              95

<210> SEQ ID NO 74
<211> LENGTH: 95
<212> TYPE: DNA
<213> ORGANISM: Homo sapiens

<400> SEQUENCE: 74
tttccaaagt attgtttaaa agtaacgaac attcagacca gctcacaaga aaatactgct    60
atacgtactc cagaacattt aatatcccaa aaagg                              95

<210> SEQ ID NO 75
<211> LENGTH: 100
<212> TYPE: DNA
<213> ORGANISM: Homo sapiens

<400> SEQUENCE: 75
acaatatcct actagtttag cttgtgttga aattgtaaat accttggcat gagataatca    60
aaagaaactg agcaagcctc agtcaattaa tactgtatct                        100

<210> SEQ ID NO 76
<211> LENGTH: 99
<212> TYPE: DNA
<213> ORGANISM: Homo sapiens

<400> SEQUENCE: 76
aattagcatg tgagaccatt gagatcacag ctgccccaaa gtgtaaagaa tgcagaattc    60
tctcaataat gataaaaacc ttgtttctat tgagactgt                          99

<210> SEQ ID NO 77
<211> LENGTH: 101
<212> TYPE: DNA
<213> ORGANISM: Homo sapiens

<400> SEQUENCE: 77
tttgttctac ttactccaaa gattcagaaa actactttga aacagaagca ggtagaaatt    60
gctaaagctt ttatggaaga tgatgaactg acagattcta a                      101

<210> SEQ ID NO 78
<211> LENGTH: 95
<212> TYPE: DNA
<213> ORGANISM: Homo sapiens

<400> SEQUENCE: 78
ttcctgtgaa aacaaatata gaagtttgtt ctacttactc caaagattca ctactttgaa    60
acagaagcag tagaaattgc taaagctttt atgga                              95

<210> SEQ ID NO 79
<211> LENGTH: 99
<212> TYPE: DNA
<213> ORGANISM: Homo sapiens

<400> SEQUENCE: 79
acacaggtga taaacaagca acccaagtgt caattaaaaa agatttggtt atgttcttgc    60
agaggagaac aaaaatagtg taaagcagca tataaaaat                          99

<210> SEQ ID NO 80

<211> LENGTH: 96
<212> TYPE: DNA
<213> ORGANISM: Homo sapiens

<400> SEQUENCE: 80
ctgcagcatg tcacccagta caacattcaa aagtggaata cagtgatact ttcaatccca    60
gaaaagtctt ttatatgatc atgaaaatgc cagcac                             96

<210> SEQ ID NO 81
<211> LENGTH: 99
<212> TYPE: DNA
<213> ORGANISM: Homo sapiens

<400> SEQUENCE: 81
cgaagattgt ttatgcatca tgtttcttta gagccgatta cctgtgtacc tttcggtaag    60
acatgtttaa attttctaa attctaatac agtatgaga                           99

<210> SEQ ID NO 82
<211> LENGTH: 98
<212> TYPE: DNA
<213> ORGANISM: Homo sapiens

<400> SEQUENCE: 82
acagacaaaa gcaaacatt gatggacatg gctctgatga tagtaaaaat gattaatgac    60
aatgagattc atcagtttaa caaaaacaac tccaatca                           98

<210> SEQ ID NO 83
<211> LENGTH: 100
<212> TYPE: DNA
<213> ORGANISM: Homo sapiens

<400> SEQUENCE: 83
cttatatatt ttctccccat tgcagcacaa ctaaggaacg tcaagagata tagaatccaa    60
attttaccgc acctggtcaa gaatttctgt ctaaatctca                         100

<210> SEQ ID NO 84
<211> LENGTH: 99
<212> TYPE: DNA
<213> ORGANISM: Homo sapiens

<400> SEQUENCE: 84
aaaaataaga ttaatgacaa tgagattcat cagtttaaca aaaacaactc aatcaagcag    60
cagctgtaac tttcacaaag tgtgaagaag aacctttag                          99

<210> SEQ ID NO 85
<211> LENGTH: 100
<212> TYPE: DNA
<213> ORGANISM: Homo sapiens

<400> SEQUENCE: 85
gagttgaaca gtgtgttagg aatattaact tggaggaaaa cagacaaaag taaaacattg    60
atggacatgg ctctgatgat agtaaaaata agattaatga                         100

<210> SEQ ID NO 86
<211> LENGTH: 100
<212> TYPE: DNA
<213> ORGANISM: Homo sapiens

<400> SEQUENCE: 86
gacatggctc tgatgatagt aaaaataaga ttaatgacaa tgagattcat tagtttaaca    60

```
aaaacaactc caatcaagca gcagctgtaa ctttcacaaa                      100
```

<210> SEQ ID NO 87
<211> LENGTH: 100
<212> TYPE: DNA
<213> ORGANISM: Homo sapiens

<400> SEQUENCE: 87

```
ccaaagtctt tgttccacct tttaaaacta aatcacattt tcacagagtt taacagtgtg   60
ttaggaatat taacttggag gaaaacagac aaaagcaaaa                        100
```

<210> SEQ ID NO 88
<211> LENGTH: 100
<212> TYPE: DNA
<213> ORGANISM: Homo sapiens

<400> SEQUENCE: 88

```
ttcagaatgc cagagatata caggatatgc gaattaagaa gaaacaaagg taacgcgtct   60
ttccacagcc aggcagtctg tatcttgcaa aaacatccac                        100
```

<210> SEQ ID NO 89
<211> LENGTH: 108
<212> TYPE: DNA
<213> ORGANISM: Homo sapiens
<220> FEATURE:
<221> NAME/KEY: misc_feature
<222> LOCATION: (51)..(58)
<223> OTHER INFORMATION: n is a, c, g, or t

<400> SEQUENCE: 89

```
ggcaacgcgt cttccacag ccaggcagtc tgtatcttgc aaaaacatcc nnnnnnnnac    60
tctgcctcga atctctctga aagcagcagt aggaggccaa gttccctc              108
```

<210> SEQ ID NO 90
<211> LENGTH: 101
<212> TYPE: DNA
<213> ORGANISM: Homo sapiens

<400> SEQUENCE: 90

```
cagccaggca gtctgtatct tgcaaaaaca tccactctgc ctcgaatctc ttctgaaagc   60
agcagtagga ggccaagttc cctctgcgtg ttctcataaa c                     101
```

<210> SEQ ID NO 91
<211> LENGTH: 101
<212> TYPE: DNA
<213> ORGANISM: Homo sapiens

<400> SEQUENCE: 91

```
attaacagca aaaatgcaga gtcttttcag tttcacactg aagattattt ttggtaagga   60
aagtttatgg actggaaaag gaatacagtt ggctgatggt g                     101
```

<210> SEQ ID NO 92
<211> LENGTH: 100
<212> TYPE: DNA
<213> ORGANISM: Homo sapiens

<400> SEQUENCE: 92

```
tggctgatgg tggatggctc ataccctcca atgatggaaa ggctggaaaa taagaatttt   60
ataggtactc tatgcaaaaa gattgtgtgt taacttttat                        100
```

<210> SEQ ID NO 93

```
<211> LENGTH: 100
<212> TYPE: DNA
<213> ORGANISM: Homo sapiens

<400> SEQUENCE: 93
ctgatggtgg atggctcata ccctccaatg atggaaaggc tggaaaagaa taattttata    60
ggtactctat gcaaaaagat tgtgtgttaa cttttatgta                         100

<210> SEQ ID NO 94
<211> LENGTH: 102
<212> TYPE: DNA
<213> ORGANISM: Homo sapiens

<400> SEQUENCE: 94
gctgtatacg tatggcgttt ctaaacattg cataaaaatt aacagcaaaa aaatgcagag    60
tcttttcagt ttcacactga agattatttt ggtaaggaaa gt                     102

<210> SEQ ID NO 95
<211> LENGTH: 96
<212> TYPE: DNA
<213> ORGANISM: Homo sapiens

<400> SEQUENCE: 95
tattttgtgt agctgtatac gtatggcgtt tctaaacatt gcataaaaat agcaaaaatg    60
cagagtcttt tcagtttcac actgaagatt attttg                             96

<210> SEQ ID NO 96
<211> LENGTH: 101
<212> TYPE: DNA
<213> ORGANISM: Homo sapiens

<400> SEQUENCE: 96
aggaatacag ttggctgatg gtggatggct cataccctcc aatgatggaa aaggctggaa    60
aagaagaatt ttataggtac tctatgcaaa aagattgtgt g                      101

<210> SEQ ID NO 97
<211> LENGTH: 100
<212> TYPE: DNA
<213> ORGANISM: Homo sapiens

<400> SEQUENCE: 97
acactgaaga ttattttggt aaggaaagtt tatggactgg aaaaggaata tagttggctg    60
atggtggatg gctcataccc tccaatgatg gaaaggctgg                        100

<210> SEQ ID NO 98
<211> LENGTH: 100
<212> TYPE: DNA
<213> ORGANISM: Homo sapiens

<400> SEQUENCE: 98
gtggatccaa agcttatttc tagaatttgg gtttataatc actatagatg aatcatatgg    60
aaactggcag ctatggaatg tgcctttcct aaggaatttg                        100

<210> SEQ ID NO 99
<211> LENGTH: 101
<212> TYPE: DNA
<213> ORGANISM: Homo sapiens

<400> SEQUENCE: 99
aagcagaaga tcggctataa aaaagataat ggaaagggat gacacagctg tcaaaacac    60
```

```
ttgttctctg tgtttctgac ataatttcat tgagcgcaaa t                 101
```

<210> SEQ ID NO 100
<211> LENGTH: 99
<212> TYPE: DNA
<213> ORGANISM: Homo sapiens

<400> SEQUENCE: 100

```
gacagttggt cagaagatta ttcttcatgg agcagaactg gtgggctctc tgatgcctgt   60
acacctcttg aagccccaga atctcttatg ttaaaggta                          99
```

<210> SEQ ID NO 101
<211> LENGTH: 99
<212> TYPE: DNA
<213> ORGANISM: Homo sapiens

<400> SEQUENCE: 101

```
gaagatcggc tataaaaaag ataatggaaa gggatgacac agctgcaaaa cacttgttct   60
ctgtgtttct gacataattt cattgagcgc aaatatatc                          99
```

<210> SEQ ID NO 102
<211> LENGTH: 98
<212> TYPE: DNA
<213> ORGANISM: Homo sapiens

<400> SEQUENCE: 102

```
ataaaaaaga taatggaaag ggatgacaca gctgcaaaaa cacttgttct gtgtttctga   60
cataatttca ttgagcgcaa atatatctga aacttcta                           98
```

<210> SEQ ID NO 103
<211> LENGTH: 100
<212> TYPE: DNA
<213> ORGANISM: Homo sapiens

<400> SEQUENCE: 103

```
gtactcggcc tgctcgctgg tataccaaac ttggattctt tcctgaccct tgaccttttc   60
ctctgccctt atcatcgctt ttcagtgatg gaggaaatgt                        100
```

<210> SEQ ID NO 104
<211> LENGTH: 100
<212> TYPE: DNA
<213> ORGANISM: Homo sapiens

<400> SEQUENCE: 104

```
tatttattaa tttgtccaga tttctgctaa cagtactcgg cctgctcgct agtataccaa   60
acttggattc tttcctgacc ctagaccttt tcctctgccc                        100
```

<210> SEQ ID NO 105
<211> LENGTH: 100
<212> TYPE: DNA
<213> ORGANISM: Homo sapiens

<400> SEQUENCE: 105

```
aaccatattt accatcacgt gcactaacaa gacagcaagt tcgtgctttg taagatggtg   60
cagagcttta tgaagcagtg aagaatgcag cagacccagc                        100
```

<210> SEQ ID NO 106
<211> LENGTH: 100
<212> TYPE: DNA
<213> ORGANISM: Homo sapiens

```
<400> SEQUENCE: 106
atctgctgaa caaaaggaac aaggtttatc aagggatgtc acaaccgtgt agaagttgcg    60
tattgtaagc tattcaaaaa agaaaaaga ttcaggtaag                          100

<210> SEQ ID NO 107
<211> LENGTH: 96
<212> TYPE: DNA
<213> ORGANISM: Homo sapiens

<400> SEQUENCE: 107
gaagagcagt taagagcctt gaataatcac aggcaaatgt tgaatgataa caagctcaga    60
tccagttgga aattaggaag gccatggaat ctgctg                             96

<210> SEQ ID NO 108
<211> LENGTH: 102
<212> TYPE: DNA
<213> ORGANISM: Homo sapiens

<400> SEQUENCE: 108
aaatgttgaa tgataagaaa caagctcaga tccagttgga aattaggaag gggccatgga    60
atctgctgaa caaaaggaac aaggtttatc aagggatgtc ac                      102

<210> SEQ ID NO 109
<211> LENGTH: 100
<212> TYPE: DNA
<213> ORGANISM: Homo sapiens

<400> SEQUENCE: 109
aaccgtgtgg aagttgcgta ttgtaagcta ttcaaaaaaa gaaaaagatt gaggtaagta    60
tgtaaatgct ttgttttat cagttttatt aacttaaaaa                          100

<210> SEQ ID NO 110
<211> LENGTH: 98
<212> TYPE: DNA
<213> ORGANISM: Homo sapiens

<400> SEQUENCE: 110
caaacagtta tactgagtat ttggcgtcca tcatcagatt tatattctct taacagaagg    60
aaagagatac agaatttatc atcttgcaac ttcaaaat                           98

<210> SEQ ID NO 111
<211> LENGTH: 99
<212> TYPE: DNA
<213> ORGANISM: Homo sapiens

<400> SEQUENCE: 111
aagagataca gaatttatca tcttgcaact tcaaaatcta aaagtaaatc gaaagagcta    60
acatacagtt agcagcgaca aaaaaaactc agtatcaac                          99

<210> SEQ ID NO 112
<211> LENGTH: 100
<212> TYPE: DNA
<213> ORGANISM: Homo sapiens

<400> SEQUENCE: 112
catctttctc caaacagtta tactgagtat ttggcgtcca tcatcagatt aatattctct    60
gttaacagaa ggaaagagat acagaattta tcatcttgca                         100

<210> SEQ ID NO 113
```

```
<211> LENGTH: 119
<212> TYPE: DNA
<213> ORGANISM: Homo sapiens
<220> FEATURE:
<221> NAME/KEY: misc_feature
<222> LOCATION: (51)..(69)
<223> OTHER INFORMATION: n is a, c, g, or t

<400> SEQUENCE: 113
tctaaaagta aatctgaaag agctaacata cagttagcag cgacaaaaaa nnnnnnnnn    60 nnnnnnnna actcagtatc aacaactacc ggtacaaacc tttcattgta attttttcag   119

<210> SEQ ID NO 114
<211> LENGTH: 100
<212> TYPE: DNA
<213> ORGANISM: Homo sapiens

<400> SEQUENCE: 114
ctttctcatc tttctccaaa cagttatact gagtatttgg cgtccatcat gagatttata    60
ttctctgtta acagaaggaa agagatacag aatttatcat                         100

<210> SEQ ID NO 115
<211> LENGTH: 100
<212> TYPE: DNA
<213> ORGANISM: Homo sapiens

<400> SEQUENCE: 115
ttccattgca tctttctcat ctttctccaa acagttatac tgagtatttg acgtccatca    60
tcagatttat attctctgtt aacagaagga aagagataca                         100

<210> SEQ ID NO 116
<211> LENGTH: 99
<212> TYPE: DNA
<213> ORGANISM: Homo sapiens

<400> SEQUENCE: 116
acttcttcca ttgcatcttt ctcatctttc tccaaacagt tatactgagt tttggcgtcc    60
atcatcagat ttatattctc tgttaacaga aggaaagag                           99

<210> SEQ ID NO 117
<211> LENGTH: 100
<212> TYPE: DNA
<213> ORGANISM: Homo sapiens

<400> SEQUENCE: 117
tggaatctcc atatgttgaa tttttgtttt gttttctgta ggtttcagat taaattttat    60
ttcagattta ccagccacgg gagccccttc acttcagcaa                         100

<210> SEQ ID NO 118
<211> LENGTH: 99
<212> TYPE: DNA
<213> ORGANISM: Homo sapiens

<400> SEQUENCE: 118
atttttagat ccagactttc agccatcttg ttctgaggtg gacctaatag atttgtcgtt    60
tctgttgtga aaaaacagg taatgcacaa tatagttaa                            99

<210> SEQ ID NO 119
<211> LENGTH: 107
<212> TYPE: DNA
<213> ORGANISM: Homo sapiens
<220> FEATURE:
```

```
<221> NAME/KEY: misc_feature
<222> LOCATION: (51)..(57)
<223> OTHER INFORMATION: n is a, c, g, or t

<400> SEQUENCE: 119
tctaacacat ctataataac attcttttct ttttttttcca ttctaggact nnnnnnntgc    60 cccttttcgtc tatttgtcag acgaatgtta caatttactg gcaataa                 107

<210> SEQ ID NO 120
<211> LENGTH: 104
<212> TYPE: DNA
<213> ORGANISM: Homo sapiens

<400> SEQUENCE: 120
agcaacctcc agtggcgacc agaatccaaa tcaggccttc ttactttatt attttgctgg    60 agattttttct gtgttttctg ctagtccaaa agagggccac tttc                    104

<210> SEQ ID NO 121
<211> LENGTH: 101
<212> TYPE: DNA
<213> ORGANISM: Homo sapiens

<400> SEQUENCE: 121
aagagggcca ctttcaagag acattcaaca aaatgaaaaa tactgttgag ggtaaggtta    60
cttttcagca tcaccacaca ttttggtatt tttctatttt g                        101

<210> SEQ ID NO 122
<211> LENGTH: 100
<212> TYPE: DNA
<213> ORGANISM: Homo sapiens

<400> SEQUENCE: 122
attcttttct ttttttcca ttctaggact tgcccctttc gtctatttgt gagacgaatg     60
ttacaattta ctggcaataa agttttggat agaccttaat                          100

<210> SEQ ID NO 123
<211> LENGTH: 101
<212> TYPE: DNA
<213> ORGANISM: Homo sapiens

<400> SEQUENCE: 123
ttgctgcaag caacctccag tggcgaccag aatccaaatc aggccttctt aactttattt    60
gctggagatt tttctgtgtt ttctgctagt ccaaaagagg g                        101

<210> SEQ ID NO 124
<211> LENGTH: 101
<212> TYPE: DNA
<213> ORGANISM: Homo sapiens

<400> SEQUENCE: 124
tgcaagcaac ctccagtggc gaccagaatc caaatcaggc cttcttactt ttatttgctg    60
gagatttttc tgtgttttct gctagtccaa aagagggcca c                        101

<210> SEQ ID NO 125
<211> LENGTH: 99
<212> TYPE: DNA
<213> ORGANISM: Homo sapiens

<400> SEQUENCE: 125
ttaatgagga cattattaag cctcatatgt taattgctgc aagcaacctc agtggcgacc    60
```

```
agaatccaaa tcaggccttc ttactttatt tgctggaga                                    99

<210> SEQ ID NO 126
<211> LENGTH: 101
<212> TYPE: DNA
<213> ORGANISM: Homo sapiens

<400> SEQUENCE: 126
tcagacgaat gttacaattt actggcaata aagttttgga tagaccttaa ttgaggacat            60
tattaagcct catatgttaa ttgctgcaag caacctccag t                               101

<210> SEQ ID NO 127
<211> LENGTH: 100
<212> TYPE: DNA
<213> ORGANISM: Homo sapiens

<400> SEQUENCE: 127 ttaccccccag tggtatgtgg gagtttgttt catacaccaa agtttgtgaa tgtaaatatt           60
ctacctggtt tatttttatg acttagtaat tgagaatttg                                 100

<210> SEQ ID NO 128
<211> LENGTH: 67
<212> TYPE: DNA
<213> ORGANISM: Homo sapiens

<400> SEQUENCE: 128
tatcttacag tcagaaatga agaagcatct gaaactgtat ttcctcatga gactgttgaa           60
attgcta                                                                     67

<210> SEQ ID NO 129
<211> LENGTH: 100
<212> TYPE: DNA
<213> ORGANISM: Homo sapiens

<400> SEQUENCE: 129
aatagaaaat caagaaaaat ccttaaaggc ttcaaaaagc actccagatg ataaaattag           60 cttttttattt atatctgttc tccctctata ggtatggtat                                100

<210> SEQ ID NO 130
<211> LENGTH: 100
<212> TYPE: DNA
<213> ORGANISM: Homo sapiens

<400> SEQUENCE: 130
gatattctct tagattttaa ctaatatgta atataaaata attgtttcct cggcacaata           60
aaagatcgaa gattgtttat gcatcatgtt tctttagagc                                 100

<210> SEQ ID NO 131
<211> LENGTH: 100
<212> TYPE: DNA
<213> ORGANISM: Homo sapiens

<400> SEQUENCE: 131
tcctgatgcc tgtacacctc ttgaagcccc agaatctctt atgttaaagg caaattaatt           60
tgcactcttg gtaaaaatca gtcattgatt cagttaaatt                                 100

<210> SEQ ID NO 132
<211> LENGTH: 100
<212> TYPE: DNA
<213> ORGANISM: Homo sapiens
```

<400> SEQUENCE: 132
cttgaatgtt atatatgtga cttttttggt gtgtgtaaca cattattaca atggatggag    60
aagacatcat ctggattata catatttcgc aatgaaagag                         100

<210> SEQ ID NO 133
<211> LENGTH: 100
<212> TYPE: DNA
<213> ORGANISM: Homo sapiens

<400> SEQUENCE: 133
tacctcagtc acataataag gaatgcatcc ctgtgtaagt gcattttggt tttctgtttt    60
gcagacttat ttaccaagca ttggaggaat atcgtaggta                         100

<210> SEQ ID NO 134
<211> LENGTH: 100
<212> TYPE: DNA
<213> ORGANISM: Homo sapiens

<400> SEQUENCE: 134
tcagtcacat aataaggaat gcatccctgt gtaagtgcat tttggtcttc cgttttgcag    60
acttatttac caagcattgg aggaatatcg taggtaaaaa                         100

<210> SEQ ID NO 135
<211> LENGTH: 100
<212> TYPE: DNA
<213> ORGANISM: Homo sapiens

<400> SEQUENCE: 135
ttctgaacct gcagaagaat ctgaacataa aaacaacaat tacgaaccaa gcctatttaa    60
aactccacaa aggaaaccat cttataatca gctggcttca                         100

<210> SEQ ID NO 136
<211> LENGTH: 108
<212> TYPE: DNA
<213> ORGANISM: Homo sapiens
<220> FEATURE:
<221> NAME/KEY: misc_feature
<222> LOCATION: (51)..(58)
<223> OTHER INFORMATION: n is a, c, g, or t

<400> SEQUENCE: 136
cacttccaaa gaatgcaaat ttataatcca gagtatatac attctcactg nnnnnnnnaa    60
ttattgtact gtttcaggaa ggaatgttcc caatagtaga cataaaag               108

<210> SEQ ID NO 137
<211> LENGTH: 100
<212> TYPE: DNA
<213> ORGANISM: Homo sapiens

<400> SEQUENCE: 137
gcatcttgaa tctcatacag actgcattct tgcagtaaag caggcaatat gtggaacttc    60
tccagtggct tcttcatttc agggtatcaa aaagtctata                         100

<210> SEQ ID NO 138
<211> LENGTH: 100
<212> TYPE: DNA
<213> ORGANISM: Homo sapiens

<400> SEQUENCE: 138
ttcatttcag ggtatcaaaa agtctatatt cagaataaga gaatcaccta gagagacttt    60

| | |
|---|---|
| caatgcaagt ttttcaggtc atatgactga tccaaacttt | 100 |

<210> SEQ ID NO 139
<211> LENGTH: 100
<212> TYPE: DNA
<213> ORGANISM: Homo sapiens

<400> SEQUENCE: 139

| | |
|---|---|
| agagcagcat cttgaatctc atacagactg cattcttgca gtaaagcagg aaatatctgg | 60 |
| aacttctcca gtggcttctt catttcaggg tatcaaaaag | 100 |

<210> SEQ ID NO 140
<211> LENGTH: 100
<212> TYPE: DNA
<213> ORGANISM: Homo sapiens

<400> SEQUENCE: 140

| | |
|---|---|
| aaaaattttc catgaagcaa acgctgatga atgtgaaaaa tctaaaaacc gagtgaaaga | 60 |
| aaaatactca tttgtatctg aagtggaacc aaatgatact | 100 |

<210> SEQ ID NO 141
<211> LENGTH: 100
<212> TYPE: DNA
<213> ORGANISM: Homo sapiens

<400> SEQUENCE: 141

| | |
|---|---|
| ccaaaaggc ttttcatata atgtggtaaa ttcatctgct ttctctggat gtagtacagc | 60 |
| aagtggaaag caagtttcca ttttagaaag ttccttacac | 100 |

<210> SEQ ID NO 142
<211> LENGTH: 100
<212> TYPE: DNA
<213> ORGANISM: Homo sapiens

<400> SEQUENCE: 142

| | |
|---|---|
| gtgatgaaaa gatcaaagaa cctactctgt tgggttttca tacagctagc aggaaaaaag | 60 |
| ttaaaattgc aaaggaatct ttggacaaag tgaaaaacct | 100 |

<210> SEQ ID NO 143
<211> LENGTH: 100
<212> TYPE: DNA
<213> ORGANISM: Homo sapiens

<400> SEQUENCE: 143

| | |
|---|---|
| aatgtagcac gcattcacat aaggtttttg ctgacattca gagtgaagaa gttttacaac | 60 |
| ataaccaaaa tatgtctgga ttggagaaag tttctaaaat | 100 |

<210> SEQ ID NO 144
<211> LENGTH: 100
<212> TYPE: DNA
<213> ORGANISM: Homo sapiens

<400> SEQUENCE: 144

| | |
|---|---|
| cgaaaattat ggcaggttgt tacgaggcat tgatgattc agaggatatt gttcataact | 60 |
| ctctagataa tgatgaatgt agcacgcatt cacataaggt | 100 |

<210> SEQ ID NO 145
<211> LENGTH: 100
<212> TYPE: DNA
<213> ORGANISM: Homo sapiens -continued

```
<400> SEQUENCE: 145
cttaaatgtt gaaggtggtt cttcagaaaa taatcactct attaaagttt atccatatct    60
ctctcaattt caacaagaca aacaacagtt ggtattagga                          100

<210> SEQ ID NO 146
<211> LENGTH: 100
<212> TYPE: DNA
<213> ORGANISM: Homo sapiens

<400> SEQUENCE: 146
agacttgact tgtgtaaacg aacccatttt caagaactct accatggttt catatggaga    60
cacaggtgat aaacaagcaa cccaagtgtc aattaaaaaa                          100

<210> SEQ ID NO 147
<211> LENGTH: 100
<212> TYPE: DNA
<213> ORGANISM: Homo sapiens

<400> SEQUENCE: 147
tttaaaatcg acatctcct tgaatataga taaaatacca gaaaaaaata ttgattacat     60
gaacaaatgg gcaggactct taggtccaat ttcaaatcac                          100

<210> SEQ ID NO 148
<211> LENGTH: 100
<212> TYPE: DNA
<213> ORGANISM: Homo sapiens

<400> SEQUENCE: 148
tcttcactat tcacctacgt ctagacaaaa tgtatcaaaa atacttcctc atgttgataa    60
gagaaaccca gagcactgtg taaactcaga atggaaaaa                           100

<210> SEQ ID NO 149
<211> LENGTH: 100
<212> TYPE: DNA
<213> ORGANISM: Homo sapiens

<400> SEQUENCE: 149
gatttagtac agcaagtgga aagcaagttt ccattttaga aagttcctta aacaaagtta    60
agggagtgtt agaggaattt gatttaatca gaactgagca                          100

<210> SEQ ID NO 150
<211> LENGTH: 100
<212> TYPE: DNA
<213> ORGANISM: Homo sapiens

<400> SEQUENCE: 150
gattaaagaa gatttgtcag atttaacttt tttggaagtt gcgaaagctc gagaagcatg    60
tcatggtaat acttcaaata aagaacagtt aactgctact                          100

<210> SEQ ID NO 151
<211> LENGTH: 100
<212> TYPE: DNA
<213> ORGANISM: Homo sapiens

<400> SEQUENCE: 151
aaatggaaaa aacctgcagt aaagaattta aattatcaaa taacttaaat tttgaaggtg    60
gttcttcaga aaataatcac tctattaaag tttctccata                          100

<210> SEQ ID NO 152
```

-continued

```
<211> LENGTH: 100
<212> TYPE: DNA
<213> ORGANISM: Homo sapiens

<400> SEQUENCE: 152
agttgtagta gaaaaacttc tgtgagtcag acttcattac ttgaagcaaa caaatggctt    60
agagaaggaa tatttgatgg tcaaccagaa agaataaata                          100

<210> SEQ ID NO 153
<211> LENGTH: 100
<212> TYPE: DNA
<213> ORGANISM: Homo sapiens

<400> SEQUENCE: 153
aaccaagcta catattgcag aagagtacat ttgaagtgcc tgaaaaccag gtgactatct    60
taaagaccac ttctgaggaa tgcagagatg ctgatcttca                          100

<210> SEQ ID NO 154
<211> LENGTH: 100
<212> TYPE: DNA
<213> ORGANISM: Homo sapiens

<400> SEQUENCE: 154
tattcataaa gatgaaacgg acttgctatt tactgatcag cacaacatat atcttaaatt    60
atctggccag tttatgaagg agggaaacac tcagattaaa                          100

<210> SEQ ID NO 155
<211> LENGTH: 100
<212> TYPE: DNA
<213> ORGANISM: Homo sapiens

<400> SEQUENCE: 155
tctcagacaa tgagaataat tttgtcttcc aagtagctaa tgaaaggaat gatcttgctt    60
taggaaatac taaggaactt catgaaacag acttgacttg                          100

<210> SEQ ID NO 156
<211> LENGTH: 100
<212> TYPE: DNA
<213> ORGANISM: Homo sapiens

<400> SEQUENCE: 156
taacttagaa tttgatggca gtgattcaag taaaaatgat actgtttgta ctcataaaga    60
tgaaacggac ttgctattta ctgatcagca caacatatgt                          100

<210> SEQ ID NO 157
<211> LENGTH: 100
<212> TYPE: DNA
<213> ORGANISM: Homo sapiens

<400> SEQUENCE: 157
taatattgaa atgactactg gcacttttgt tgaagaaatt actgaaaatt gcaagagaaa    60
tactgaaaat gaagataaca aatatactgc tgccagtaga                          100

<210> SEQ ID NO 158
<211> LENGTH: 100
<212> TYPE: DNA
<213> ORGANISM: Homo sapiens

<400> SEQUENCE: 158
gataatagaa aatcaagaaa aatccttaaa ggcttcaaaa agcactccag ttggtaaaat    60
```

```
tagcttttta tttatatctg ttctccctct ataggtatgg                 100
```

<210> SEQ ID NO 159
<211> LENGTH: 100
<212> TYPE: DNA
<213> ORGANISM: Homo sapiens

<400> SEQUENCE: 159

```
ctttggaaaa atcttcaagc aatttagcag tttcaggaca tccattttat aaagtttctg    60
ctacaagaaa tgaaaaaatg agacacttga ttactacagg                        100
```

<210> SEQ ID NO 160
<211> LENGTH: 100
<212> TYPE: DNA
<213> ORGANISM: Homo sapiens

<400> SEQUENCE: 160

```
ctggccaggg gttgtgcttt ttaaatttca attttatttt tgctaagtat gtattctttg    60
atagatttaa ttacaagtct tcagaatgcc agagatatac                        100
```

<210> SEQ ID NO 161
<211> LENGTH: 96
<212> TYPE: DNA
<213> ORGANISM: Homo sapiens

<400> SEQUENCE: 161

```
tttattgtgt gatacatgtt tactttaaat tgttttctt ttttgtgtgt attttgtgta    60
gctgtatacg tatggcgttt ctaaacattg cataaa                             96
```

<210> SEQ ID NO 162
<211> LENGTH: 100
<212> TYPE: DNA
<213> ORGANISM: Homo sapiens

<400> SEQUENCE: 162

```
tctagttaca atagatggaa cttttttgtt ctgattgctt tttattccaa catcttaaat    60
ggtcacaggg ttatttcagt gaagagcagt taagagcctt                        100
```

<210> SEQ ID NO 163
<211> LENGTH: 100
<212> TYPE: DNA
<213> ORGANISM: Homo sapiens

<400> SEQUENCE: 163

```
cagttttgat aagtgcttgt tagtttatgg aatctccata tgttgaattt ctgttttgtt    60
ttctgtaggt ttcagatgaa attttatttc agatttacca                        100
```

<210> SEQ ID NO 164
<211> LENGTH: 100
<212> TYPE: DNA
<213> ORGANISM: Homo sapiens

<400> SEQUENCE: 164

```
atgaaatttt atttcagatt taccagccac gggagcccct tcacttcagc gaattttag    60
atccagactt tcagccatct tgttctgagg tggacctaat                        100
```

<210> SEQ ID NO 165
<211> LENGTH: 100
<212> TYPE: DNA
<213> ORGANISM: Homo sapiens

<400> SEQUENCE: 165
cactttcaag agacattcaa caaaatgaaa aatactgttg aggtaaggtt ccttttcagc    60
atcaccacac attttggtat ttttctattt tgacagtcca    100

<210> SEQ ID NO 166
<211> LENGTH: 100
<212> TYPE: DNA
<213> ORGANISM: Homo sapiens

<400> SEQUENCE: 166
aaacaagctt atgcatatac tgcatgcaaa tgatcccaag tggtccaccc aaactaaaga    60
ctgtacttca gggccgtaca ctgctcaaat cattcctggt    100

<210> SEQ ID NO 167
<211> LENGTH: 100
<212> TYPE: DNA
<213> ORGANISM: Homo sapiens

<400> SEQUENCE: 167
aaagaaaaaa gaactgaatt ctcctcagat gactccattt aaaaaattca gtgaaatttc    60
tcttttggaa agtaattcaa tagctgacga agaacttgca    100

<210> SEQ ID NO 168
<211> LENGTH: 100
<212> TYPE: DNA
<213> ORGANISM: Homo sapiens

<400> SEQUENCE: 168
cattgataaa tacccaagct cttttgtctg gttcaacagg agaaaaacaa cttatatctg    60
tcagtgaatc cactaggact gctcccacca gttcagaaga    100

<210> SEQ ID NO 169
<211> LENGTH: 100
<212> TYPE: DNA
<213> ORGANISM: Homo sapiens

<400> SEQUENCE: 169
aaagtaattc aatagctgac gaagaacttg cattgataaa tacccaagct gttttgtctg    60
gttcaacagg agaaaaacaa tttatatctg tcagtgaatc    100

<210> SEQ ID NO 170
<211> LENGTH: 100
<212> TYPE: DNA
<213> ORGANISM: Homo sapiens

<400> SEQUENCE: 170
tctcagactg aaacgacgtt gtactacatc tctgatcaaa gaacaggaga attcccaggc    60
cagtacggaa gaatgtgaga aaaataagca ggacacaatt    100

<210> SEQ ID NO 171
<211> LENGTH: 100
<212> TYPE: DNA
<213> ORGANISM: Homo sapiens

<400> SEQUENCE: 171
cagtacggaa gaatgtgaga aaaataagca ggacacaatt acaactaaaa catatatcta    60
agcatttgca aaggcgacaa taaattattg acgcttaacc    100

<210> SEQ ID NO 172

```
<211> LENGTH: 100
<212> TYPE: DNA
<213> ORGANISM: Homo sapiens

<400> SEQUENCE: 172
gaagaatgtg agaaaaataa gcaggacaca attacaacta aaaatatat gtaagcattt    60 gcaaaggcga caataaatta ttgacgctta acctttccag                        100

<210> SEQ ID NO 173
<211> LENGTH: 100
<212> TYPE: DNA
<213> ORGANISM: Homo sapiens

<400> SEQUENCE: 173
ttcaaatgta gcacatcaga agcccttga gagtggaagt gacaaaatct tcaaggaagt    60
tgtaccgtct ttggcctgtg aatggtctca actaacccctt                       100

<210> SEQ ID NO 174
<211> LENGTH: 100
<212> TYPE: DNA
<213> ORGANISM: Homo sapiens

<400> SEQUENCE: 174
ttatgttttt ctaaatgtag aacaaaaaat ctacaaaaag taagaactag aaagactagg    60
aaaaaaattt tccatgaagc aaacgctgat gaatgtgaaa                         100

<210> SEQ ID NO 175
<211> LENGTH: 100
<212> TYPE: DNA
<213> ORGANISM: Homo sapiens

<400> SEQUENCE: 175
atctggaact tctccagtgg cttcttcatt tcagggtatc aaaaagtcta cattcagaat    60
aagagaatca cctaaagaga ctttcaatgc aagtttttca                        100

<210> SEQ ID NO 176
<211> LENGTH: 100
<212> TYPE: DNA
<213> ORGANISM: Homo sapiens

<400> SEQUENCE: 176
taatatccac tttgaaaaag aaaacaaata agtttattta tgctatacat catgaaacat    60
cttataaagg aaaaaaaata ccgaaagacc aaaaatcaga                        100

<210> SEQ ID NO 177
<211> LENGTH: 100
<212> TYPE: DNA
<213> ORGANISM: Homo sapiens

<400> SEQUENCE: 177
tttgccacgt atttctagcc taccaaaatc agagaagcca ttaaatgagg gaacagtggt    60
aaataagaga gatgaagagc agcatcttga atctcataca                        100

<210> SEQ ID NO 178
<211> LENGTH: 100
<212> TYPE: DNA
<213> ORGANISM: Homo sapiens

<400> SEQUENCE: 178
acgaacccat tttcaagaac tctaccatgg ttttatatgg agacacaggt aataaacaag    60
```

```
caacccaagt gtcaattaaa aaagatttgg tttatgttct                     100
```

<210> SEQ ID NO 179
<211> LENGTH: 100
<212> TYPE: DNA
<213> ORGANISM: Homo sapiens

<400> SEQUENCE: 179

```
acaaaatgta tcaaaaatac ttcctcgtgt tgataagaga aacccagagc gctgtgtaaa    60
ctcagaaatg gaaaaaacct gcagtaaaga atttaaatta                        100
```

<210> SEQ ID NO 180
<211> LENGTH: 100
<212> TYPE: DNA
<213> ORGANISM: Homo sapiens

<400> SEQUENCE: 180

```
agcatgtcat ggtaatactt caaataaaga acagttaact gctactaaaa tggagcaaaa    60
tataaaagat tttgagactt ctgatacatt ttttcagact                        100
```

<210> SEQ ID NO 181
<211> LENGTH: 100
<212> TYPE: DNA
<213> ORGANISM: Homo sapiens

<400> SEQUENCE: 181

```
taagatagaa aatcataatg ataaaactgt aagtgaaaaa aataataaat accaactgat    60
attacaaaat aatattgaaa tgactactgg cacttttgtt                        100
```

<210> SEQ ID NO 182
<211> LENGTH: 100
<212> TYPE: DNA
<213> ORGANISM: Homo sapiens

<400> SEQUENCE: 182

```
agatttaaaa tcggacatct ccttgaatat agataaaata ccagaaaaaa gtaatgatta    60
catgaacaaa tgggcaggac tcttaggtcc aatttcaaat                        100
```

<210> SEQ ID NO 183
<211> LENGTH: 100
<212> TYPE: DNA
<213> ORGANISM: Homo sapiens

<400> SEQUENCE: 183

```
tgaggtatat aatgattcag gatatctctc aaaaaataaa cttgattctg atattgagcc    60
agtattgaag aatgttgaag atcaaaaaaa cactagtttt                        100
```

<210> SEQ ID NO 184
<211> LENGTH: 100
<212> TYPE: DNA
<213> ORGANISM: Homo sapiens

<400> SEQUENCE: 184

```
gccaaacgaa aattatggca ggttgttacg aggcattgga tgattcagag aatattcttc    60
ataactctct agataatgat gaatgtagca cgcattcaca                        100
```

<210> SEQ ID NO 185
<211> LENGTH: 100
<212> TYPE: DNA
<213> ORGANISM: Homo sapiens

```
<400> SEQUENCE: 185
tgaacagtgt gttaggaata ttaacttgga ggaaaacaga caaaagcaaa tcattgatgg    60
acatggctct gatgatagta aaaataagat taatgacaat                         100

<210> SEQ ID NO 186
<211> LENGTH: 100
<212> TYPE: DNA
<213> ORGANISM: Homo sapiens

<400> SEQUENCE: 186
acaaaggcaa cgcgtctttc cacagccagg cagtctgtat cttgcaaaaa tatccactct    60
gcctcgaatc tctctgaaag cagcagtagg aggccaagtt                         100

<210> SEQ ID NO 187
<211> LENGTH: 100
<212> TYPE: DNA
<213> ORGANISM: Homo sapiens

<400> SEQUENCE: 187
tatctgaaac ttctagcaat aaaactagta gtgcagatac ccaaaaagtg tccattattg    60
aacttacaga tgggtggtat gctgttaagg cccagttaga                         100

<210> SEQ ID NO 188
<211> LENGTH: 100
<212> TYPE: DNA
<213> ORGANISM: Homo sapiens

<400> SEQUENCE: 188
tcctaaaata tgcattttttg ttttcacttt tagatatgat acggaaattg gtagaagcag    60
aagatcggct ataaaaaaga taatggaaag ggatgacaca                         100

<210> SEQ ID NO 189
<211> LENGTH: 100
<212> TYPE: DNA
<213> ORGANISM: Homo sapiens

<400> SEQUENCE: 189
catatttcgc aatgaaagag aggaagaaaa ggaagcagca aaatatgtgg cggcccaaca    60
aaagagacta gaagccttat tcactaaaat tcaggaggaa                         100

<210> SEQ ID NO 190
<211> LENGTH: 100
<212> TYPE: DNA
<213> ORGANISM: Homo sapiens

<400> SEQUENCE: 190 gtgactttttt tggtgtgtgt aacacattat tacagtggat ggagaagaca ccatctggat    60
tatacatatt tcgcaatgaa agagaggaag aaaaggaagc                         100

<210> SEQ ID NO 191
<211> LENGTH: 100
<212> TYPE: DNA
<213> ORGANISM: Homo sapiens

<400> SEQUENCE: 191
caaatgttga atgataagaa acaagctcag atccagttgg aaattaggaa tgccatggaa    60
tctgctgaac aaaaggaaca aggtttatca agggatgtca                         100

<210> SEQ ID NO 192
```

```
<211> LENGTH: 100
<212> TYPE: DNA
<213> ORGANISM: Homo sapiens

<400> SEQUENCE: 192
atattctctg ttaacagaag gaaagagata cagaatttat catcttgcaa tttcaaaatc      60
taaaagtaaa tctgaaagag ctaacataca gttagcagcg                           100
```